(12) United States Patent
Yamamoto et al.

(10) Patent No.: US 11,696,743 B2
(45) Date of Patent: Jul. 11, 2023

(54) ULTRASONIC OSCILLATOR UNIT HAVING ELECTRODE PART PROVIDED IN ULTRASONIC OSCILLATOR, THREE OR MORE CONNECTORS, AND THREE OR MORE ELECTRODE WIRING BOARDS MOUNTED TO THREE OR MORE CONNECTORS AND ELECTRICALLY CONNECTED TO ELECTRODE PART

(71) Applicant: FUJIFILM Corporation, Tokyo (JP)

(72) Inventors: Katsuya Yamamoto, Ashigarakami-gun (JP); Yasuhiko Morimoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1318 days.

(21) Appl. No.: 16/149,660

(22) Filed: Oct. 2, 2018

(65) Prior Publication Data
US 2019/0038257 A1    Feb. 7, 2019

Related U.S. Application Data

(63) Continuation of application No. PCT/JP2017/007414, filed on Feb. 27, 2017.

(30) Foreign Application Priority Data

Apr. 28, 2016 (JP) .................. 2016-091935

(51) Int. Cl.
*A61B 8/00* (2006.01)
*A61B 8/12* (2006.01)
*B06B 1/06* (2006.01)

(52) U.S. Cl.
CPC .............. *A61B 8/4494* (2013.01); *A61B 8/12* (2013.01); *A61B 8/445* (2013.01); *A61B 8/4488* (2013.01);
(Continued)

(58) Field of Classification Search
CPC ......... A61B 8/12; A61B 8/445; A61B 8/4488; A61B 8/4494; B06B 1/0622; B06B 1/0625; B06B 2201/76
(Continued)

(56) References Cited

U.S. PATENT DOCUMENTS

2002/0156373 A1*  10/2002  Wakabayashi ........ B06B 1/0622
                                                          600/437
2006/0241473 A1*  10/2006  Kuniyasu ................. A61B 8/12
                                                          600/459
(Continued)

FOREIGN PATENT DOCUMENTS

CN    101466314 A    6/2009
CN    102026581 A    4/2011
(Continued)

OTHER PUBLICATIONS

Chinese Office Action and Search Report dated Sep. 3, 2020 for Application No. 201780024209.3 with an English translation of the Office Action.
(Continued)

*Primary Examiner* — Shawki S Ismail
*Assistant Examiner* — Monica Mata
(74) *Attorney, Agent, or Firm* — Birch, Stewart, Kolasch & Birch, LLP

(57) ABSTRACT

An ultrasonic oscillator unit including an ultrasonic oscillator array in which a plurality of ultrasonic oscillators are arranged; an electrode part having a plurality of electrodes electrically connected to the plurality of ultrasonic oscillators, respectively; a circular-arc backing material layer disposed on a rear surface of the ultrasonic oscillator array; three or more wiring boards electrically connected to the plurality of electrodes of the electrode part; and three or more connectors to which a plurality of cables are con-
(Continued)

nected, respectively. The three or more wiring boards are respectively mounted to the three or more connectors and electrically connect the plurality of electrodes of the electrode part to the plurality of cables. The three or more connectors are arranged on a rear surface side of the backing material layer in a width direction.

22 Claims, 7 Drawing Sheets

(52) U.S. Cl.
CPC .......... B06B 1/0622 (2013.01); B06B 1/0625 (2013.01); *B06B 2201/76* (2013.01)

(58) Field of Classification Search
USPC ........................................................ 310/324
See application file for complete search history.

(56) References Cited

U.S. PATENT DOCUMENTS

| | | | |
|---|---|---|---|
| 2007/0167814 A1* | 7/2007 | Wakabayashi | ......... A61B 8/445 600/459 |
| 2009/0088646 A1 | 4/2009 | Nagano et al. | |
| 2009/0093725 A1 | 4/2009 | Sato et al. | |
| 2011/0071396 A1 | 3/2011 | Sano et al. | |
| 2011/0301413 A1 | 12/2011 | Morimoto | |
| 2011/0316389 A1 | 12/2011 | Kwon et al. | |
| 2014/0058269 A1 | 2/2014 | Irie | |
| 2016/0183914 A1 | 6/2016 | Fujimura | |
| 2018/0132820 A1 | 5/2018 | Irie | |

FOREIGN PATENT DOCUMENTS

| | | |
|---|---|---|
| CN | 102283624 A | 12/2011 |
| CN | 102297901 A | 12/2011 |
| CN | 103142244 A | 6/2013 |
| CN | 105451664 A | 3/2016 |
| JP | 7-236638 A | 9/1995 |
| JP | 8-89505 A | 4/1996 |
| JP | 2005-218518 A | 8/2005 |
| JP | 4445764 B2 | 4/2010 |
| JP | 5329065 B2 | 10/2013 |
| JP | 5399594 B1 | 1/2014 |
| WO | WO 2017/010292 A1 | 1/2017 |

OTHER PUBLICATIONS

Extended European Search Report, dated Feb. 14, 2019, for corresponding European Application No. 17789045.6.
International Preliminary Report on Patentability and Written Opinion of the International Searching Authority (forms PCT/IB/373, PCT/ISA/237 and PCT/IB/326), dated Nov. 8, 2018, for corresponding International Application No. PCT/JP2017/007414, with a Written Opinion translation.
International Search Report (form PCT/ISA/210), dated May 23, 2017, for corresponding International Application No. PCT/JP2017/007414, with an English translation.
Chinese Office Action, dated Dec. 3, 2020, for corresponding Chinese Application No. 201780024209.3, with an English translation.

* cited by examiner

ULTRASONIC OSCILLATOR UNIT HAVING ELECTRODE PART PROVIDED IN ULTRASONIC OSCILLATOR, THREE OR MORE CONNECTORS, AND THREE OR MORE ELECTRODE WIRING BOARDS MOUNTED TO THREE OR MORE CONNECTORS AND ELECTRICALLY CONNECTED TO ELECTRODE PART

CROSS-REFERENCE TO RELATED APPLICATIONS

This application is a Continuation of PCT International Application No. PCT/JP2017/007414 filed on Feb. 27, 2017, which claims priority under 35 U.S.C § 119(a) to Japanese Patent Application No. 2016-091935 filed on Apr. 28, 2016. Each of the above application(s) is hereby expressly incorporated by reference, in its entirety, into the present application.

BACKGROUND OF THE INVENTION

1. Field of the Invention

The present invention relates to an ultrasonic oscillator unit, and particularly, to an ultrasonic oscillator unit having an ultrasonic oscillator wiring structure for realizing micro ultrasonic oscillators used for an ultrasonic endoscope to be inserted into a body cavity.

2. Description of the Related Art

Ultrasonic endoscopes are ones in which an ultrasonic observation part is provided at a distal end part of an ultrasonic endoscope with observation of the gallbladder or the pancreas by an alimentary canal as a main purpose. In order to safely insert the ultrasonic endoscope into the alimentary canal, an optical sensor, an illumination unit, an air/water supply port, and a suction port in addition to the ultrasonic observation part are provided at the distal end part of the ultrasonic endoscope, similarly to ordinary endoscopes that are not provided with the ultrasonic observation part. For that reason, the external diameter of the distal end part of the ultrasonic endoscope increases, and causes a decrease in the operability of the ultrasonic endoscope and an increase in the burden on a patient into which the distal end part of the ultrasonic endoscope is to be inserted.

Thus, in order to improve the operability of the ultrasonic endoscope and mitigate the burden on the patient, the ultrasonic observation part is required to be small-sized. Thus, in recent years, various proposals, such as improving the workability in wiring task and making the ultrasonic observation part of the ultrasonic endoscope small-sized are made (refer to JP4445764B, JP5399594B, and JP5329065B).

JP4445764B discloses an ultrasonic oscillator unit having an ultrasonic oscillator array that has an acoustic matching layer, piezoelectric elements, and a rear surface damping layer; a rigid board electrically connected to the respective piezoelectric elements in the vicinity of a central part of the ultrasonic oscillator array in a width direction thereof; a signal cable bundle including a plurality of signal core wires; and a flexible printed wired board (FPC: Flexible Printed Circuit) that is interposed between the rigid board and the signal cable bundle to electrically connect both. Moreover, the ultrasonic oscillator array, and the cable bundle and the FPC are separate structures, both are connected to each other using thermocompression bonding as a means, and thereafter, the FPC is configured in a multiple-folded form.

JP5399594B discloses an ultrasonic endoscope having an ultrasonic transmission/reception unit that transmits and receives ultrasonic waves; a wiring board electrically connected to a rear surface side of the ultrasonic transmission/reception unit; a plurality of driver wires electrically connected to the wiring board; and a housing that houses the wiring board to hold the ultrasonic transmission/reception unit. The wiring board has a rigid circuit board electrically connected to a plurality of ultrasonic oscillators in the vicinity of central parts thereof in a width direction; and an enveloping part that wraps and bundles the driver wires, and is inserted into a housing in a state where the driver wires are wrapped and bundled by the enveloping part.

JP5329065B discloses a convex ultrasound probe of an ultrasonic endoscope in which a plurality of ultrasonic transducers (ultrasonic oscillators) arranged as a multi-row array on a convex surface of a backing material, and a plurality of shielding wires (cables) are connected to each other by an FPC disposed on a sides surface of the backing material, and a rear surface of the backing material made of elastomer, such as rubber, and a sheathing member (case) at a distal end of an insertion part of an ultrasonic endoscope made of, for example, stainless steel (SUS304) or the like are connected to each other by a heat-conduction member made of, for example, aluminum nitride (AlN) or the like.

SUMMARY OF THE INVENTION

Meanwhile, in the ultrasonic endoscopes disclosed in JP4445764B, JP5399594B, and JP5329065B, numerous ultrasonic oscillators are disposed in an array on the ultrasonic observation part provided at a distal end part, and cables are respectively wired to the ultrasonic oscillator. For example, the number of channels is as large as, for example, 48 to 192, the external diameter of ultrasonic observation part is small, and expensive, extremely fine cables are used as the cables. Therefore, in the current situation, wiring within the ultrasonic observation part is a complicated task, and numerous wiring lines are manually wired within a small distal end part. For this reason, the handling of the cables within the ultrasonic observation part with a small external diameter is complicated, and high filling is required. That is, since it is necessary to wire the cables in high density within the ultrasonic observation part in addition to the handling of the cables being complicated, this becomes a causer that the workability is poor and the manufacturing costs of the ultrasonic endoscope become high.

In spite of size reduction of the ultrasonic observation part being required in order to improve the operability and reduce the burden on the patient, as described above, there is a problem that the size reduction of the ultrasonic observation part is very difficult from viewpoints of the manufacture stability of the ultrasonic observation part, and the manufacturing costs thereof.

Additionally, in the techniques disclosed in JP4445764B and JP5329065B, a structure in which the FPC of the ultrasonic oscillator unit is folded up is provided. Therefore, there is problem that the wiring structure of the cable bundle and the FPC is complicated. Additionally, although the ultrasonic oscillator array, and the cable bundle and the FPC are connected to each other by thermocompression bonding, there is still a problem in the workability of the wiring. Particularly, in JP4445764B, there are problems that, during the manufacture of the ultrasonic oscillator unit, a burden, for example, a load is applied on a cable in a case where the FPC is folded up multiple times, and the cable wiring line to which the load is applied is disconnected.

Additionally, in the technique disclosed in JP5399594B, the workability of the wiring task is reduced by using a simple configuration. However, inspection of the quality of the ultrasonic oscillators used for the ultrasonic endoscope is allowed for the first time after the wiring between the ultrasonic oscillators and the cables is completed. For this reason, since there is a constant yield rate, in a case where there a problem in the quality of the ultrasonic oscillators, all components and materials that are used for the ultrasonic oscillator and the wiring lines of the ultrasonic oscillators, such as a large number of wired fine and expensive cables, cannot be used and become useless. Therefore, there is a problem that loss is large and the manufacturing costs of the ultrasonic endoscope become high.

Additionally, since the upper limit of the output of the ultrasonic oscillators is defined by a temperature rise value of an acoustic lens surface, in the technique disclosed in JP5329065B, it is possible to output a higher output by connecting the backing material and the case to each other by the heat-conduction member to improve the heat dissipation performance of the ultrasonic oscillators. However, in the technique disclosed in JP5329065B, since only a heat dissipation path along which the heat generated the ultrasonic oscillator is dissipated to the case via the backing material and the heat-conduction member is taken into consideration, there is a problem that further improvement in the heat dissipation effect cannot be expected.

Additionally, in any of the techniques disclosed in JP4445764B, JP5399594B, and JP5329065B, the electrodes of the ultrasonic oscillator array and the wiring board, such as the FPC, a printed circuit board (PCB), or a printed wired board (PWB), are electrically connected to each other in the vicinity of the central part of the ultrasonic oscillator array in the width direction thereof. In this structure, there are problems that the manufacture is significantly difficult and the success rate of the manufacture is not high.

Additionally, in the related-art structures disclosed in JP4445764B, JP5399594B, and JP5329065B, a wiring board or wiring boards are disposed on one or both of sides surfaces of the backing material. Therefore, in a case where the number of channels increases as described above, there are problems in that the number of cable wiring lines per one wiring board increases, and a wiring structure around a cable soldering part for connecting the cables are complicated.

Additionally, as in the techniques disclosed in JP4445764B and JP5399594B, in the related-art structures in which the two wiring boards are respectively disposed on both side surfaces of the backing material, and a gap between the backing material and the case is filled with the filler, there is only the heat dissipation path along which the heat generated in the ultrasonic oscillators is dissipated to the case via the backing material and the filler. Therefore, there is a problem that further improvement in the heat dissipation effect cannot be expected.

An object of the invention is to solve the above problems of the related arts and to provide an ultrasonic oscillator unit that can be small-sized, has excellent workability in a case where respective electrodes of an ultrasonic oscillator array and numerous cables are wired, has low difficulty of an operation step, has a wiring structure in which a load on a cable is unlikely to occur and there is less risk of disconnection, allows further improvement in a heat dissipation effect from the ultrasonic oscillator array generating heat to be expected, and is suitable for use in an ultrasonic endoscope, and. Additionally, another object of the invention is to solve the above problems of the related arts and to provide an ultrasonic oscillator unit that is capable of inspecting an ultrasonic oscillator array before cable wiring, has high manufacture stability, and does not cause an increase in cost, and is suitable for use in an ultrasonic endoscope, in addition to the above object.

In order to achieve the above object, an ultrasonic oscillator unit comprises an ultrasonic oscillator array in which a plurality of ultrasonic oscillators having a rod shape are arranged in a circular-arc shape while aligning in a longitudinal direction of the rod shape; an electrode part that is provided in at least one end surface of the plurality of ultrasonic oscillators perpendicular to the longitudinal direction and has a plurality of electrodes electrically connected to the plurality of ultrasonic oscillators, respectively; a circular-arc backing material layer disposed on a rear surface of the ultrasonic oscillator array that becomes a center side of the circular-arc shape; three or more electrode wiring boards electrically connected to the plurality of electrodes of the electrode part; and three or more connectors to which the plurality of cables are connected, respectively. The three or more electrode wiring boards are respectively mounted to the three or more connectors and electrically connect the plurality of electrodes of the electrode part to the plurality of cables. The three or more connectors are arranged in a width direction of the backing material layer in the longitudinal direction on a rear surface side of the backing material layer opposite to the ultrasonic oscillator array.

Here, it is preferable that the ultrasonic oscillator unit further comprises three or more cable wiring boards each including a cable wiring part to which the plurality of cables are connected, and the respective cable wiring parts of the three or more cable wiring boards and the three or more electrode wiring boards are respectively connected to each other by the three or more connectors.

Additionally, it is preferable that the backing material layer has an outer surface having a circular-arc cross-section on the rear surface of the ultrasonic oscillator array and has a recess on a side opposite to the outer surface, and at least portions of the three or more connectors are disposed within the recess of the backing layer.

Additionally, it is preferable that the backing material layer has a semicircular columnar shape, a shape obtained by cutting a column with a plane parallel to a centerline of the column, a semicylindrical shape, or a bow shape, and a bottom surface of the backing material layer is one continuous plane located on the same plane or two separated planes located on the same plane.

Additionally, it is preferable that the recess of the backing material layer is provided from an outer side surface of the backing material layer in the width direction thereof toward a center side thereof in the width direction.

Additionally, it is preferable that the recess of the backing material layer is either a through-hole penetrating from one outer side surface of two outer side surfaces of the backing material layer on both sides in the width direction thereof to the other outer side surface thereof, or a counterbore recessed from at least one outer side surface of the backing material layer in the width direction thereof toward the center side thereof in the width direction.

Additionally, it is preferable that the through-hole has a cross-sectional shape hollowed out in a rectangular shape, a polygonal shape, or a circular shape, the counterbore is formed from at least one outer side surface of the backing material layer in the width direction thereof toward the center side thereof in the width direction, and the counterbore is a rectangular counterbore, a polygonal counterbore, a bow-shaped counterbore, a semicircular counterbore, a pyramidal counterbore, or a conical counterbore.

Additionally, it is preferable that the recess of the backing material layer is a through-hole having a shape hollowed out in a rectangular shape.

Additionally, it is preferable that two connectors of the three or more connectors are respectively disposed on two outer side surface sides on both sides in the width direction of the backing material layer, within the recess of the backing material layer, and one or more remaining connectors of the three or more connectors are disposed between the two connectors within the recess of the backing material layer.

Additionally, it is preferable that the ultrasonic oscillator unit further comprises a filler layer, made of a heat-conduction member, which fills a gap of the recess between at least one connector of the three or more connectors, the three or more electrode wiring boards, and the plurality of cables, which are housed in the recess of the backing material layer, and the backing material layer.

Additionally, it is preferable that the ultrasonic oscillator unit further comprises a filler layer, made of a heat-conduction member, which covers at least portions of the three or more electrode wiring boards, the three or more connectors, and the plurality of cables.

Additionally, it is preferable that, in a case where an acoustic impedance of the filler layer is defined as Zp and an acoustic impedance of the backing material layer is defined as Zb, an acoustic impedance reflectivity Q between the filler layer and the backing material layer, which is expressed using the following Equation (1) is 50% or less.

$$Q = 100 \times |Zp - Zb| / (Zp + Zb) \qquad (1)$$

Here, the unit of the acoustic impedance Zp and Zb is $kg/(m^2 \cdot s)$.

Additionally, it is preferable that a thermal conductivity of the filler layer is equal to or more than $1.0 \ W/m \cdot K$.

Additionally, it is preferable that the electrode wiring boards are flexible printed wired boards or rigid printed circuit boards.

Additionally, it is preferable that the electrode wiring boards are electrically connected to the electrode part via heat fusion connection, and are disposed on outer side surface, in the width direction, of the ultrasonic oscillator array in the longitudinal direction.

According to the invention, it is possible to provide the ultrasonic oscillator unit that can be small-sized, has excellent workability in a case where the respective electrodes of the ultrasonic oscillator array and numerous cables are wired and low difficulty of the operation step, has a wiring structure in which a load on a cable is unlikely to occur and there is less risk of disconnection, can expect further improvement in the heat dissipation effect from the ultrasonic oscillator array generating heat, and is suitable for use in the ultrasonic endoscope. According to the invention, in addition to the above effects, it is also possible to provide the ultrasonic oscillator unit that is capable of inspecting the ultrasonic oscillator array before cable wiring, has high manufacture stability, and does not cause an increase in cost, and is suitable for use in the ultrasonic endoscope.

DESCRIPTION OF THE PREFERRED EMBODIMENTS

An ultrasonic oscillator unit related to the invention will be described below in detail on the basis of preferred embodiments illustrated in the accompanying drawings.

Figure 1:
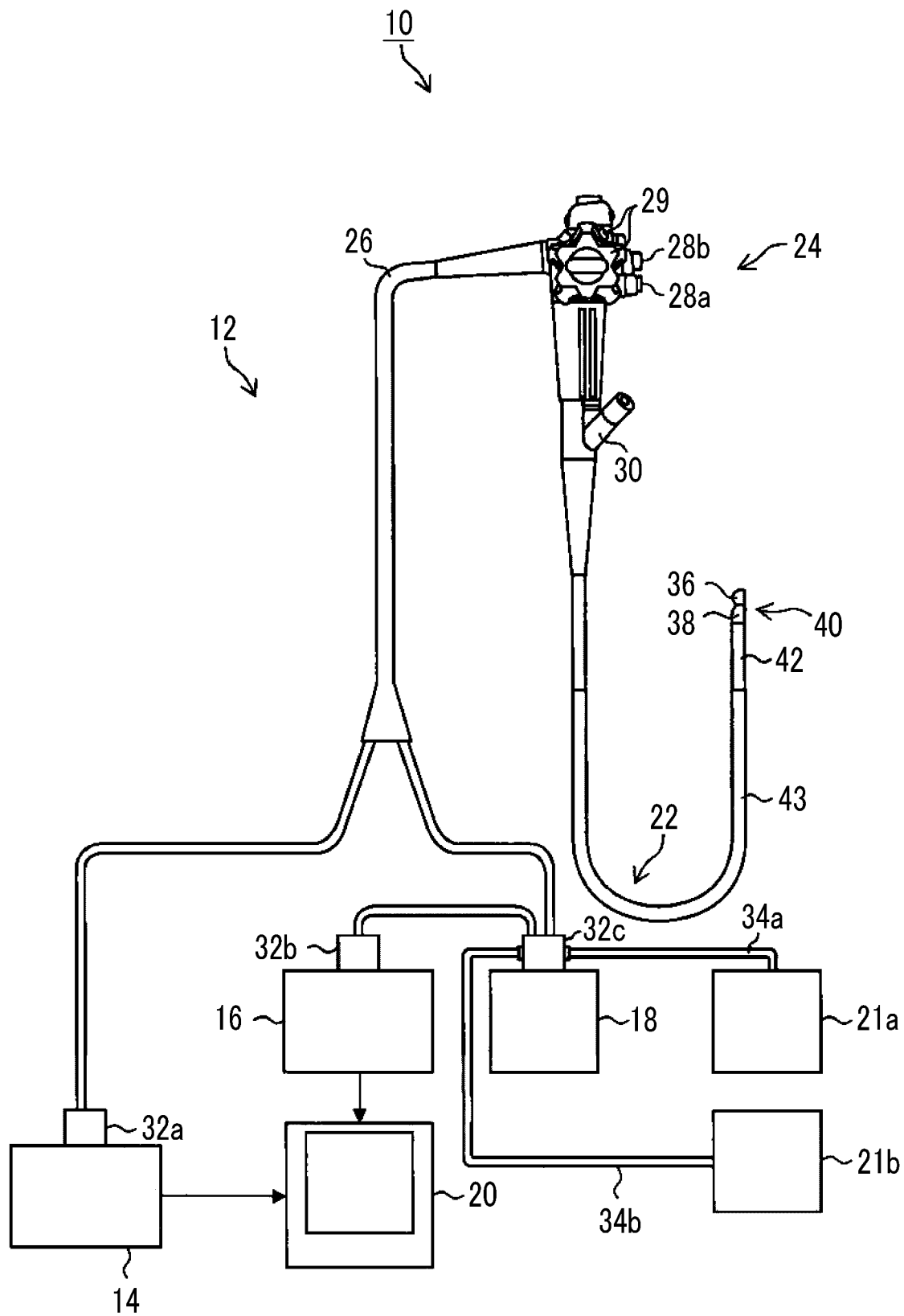
FIG. 1 is a schematic configuration view illustrating an example of the configuration of an ultrasonic inspection system using an ultrasonic endoscope to which an ultrasonic oscillator unit of the invention is applied.

FIG. 1 is a schematic configuration view illustrating an example of the configuration of an ultrasonic inspection system using the ultrasonic endoscope using the ultrasonic oscillator unit of the invention.

An ultrasonic inspection system 10 illustrated in FIG. 1 allows observation of the gallbladder or the pancreas that is difficult in the ultrasonic inspection from the body surface of a subject, such as a patient, via alimentary canals, such as the esophagus, the stomach, the duodenum, the small intestine, and the large intestine that are body cavities of the subject, includes the ultrasonic oscillator unit of the invention, and acquires an ultrasound image of a region to be observed of the subject while inserting the ultrasonic endoscope of the invention having an ultrasonic observation part and an endoscope observation part into the body cavities of the subject to observe an endoscopic image of the subject. The ultrasonic observation part acquires an ultrasonic tomographic image (hereinafter referred to as the ultrasound image), and the endoscope observation part acquires an endoscopic optical image (hereinafter referred to as the endoscopic image).

As illustrated in FIG. 1, the ultrasonic inspection system 10 is configured to include an ultrasonic endoscope 12 using an ultrasonic oscillator unit (46: refer to FIGS. 2 to 5) of the invention, an ultrasonic wave processor device 14 that creates the ultrasound image, an endoscope processor device 16 that creates the endoscopic image, a light source device 18 that supplies the illumination light for illuminating the inside of a body cavity to the ultrasonic endoscope 12, and a monitor 20 that displays the ultrasound image and/or the endoscopic image.

Additionally, the ultrasonic inspection system 10 further includes a water supply tank 21a that stores washing water or the like, and a suction pump 21b that suctions a suction object (including the supplied washing water) within the body cavity. In addition, although not illustrated, the ultrasonic inspection system 10 may further include a supply pump that supplies washing water within the water supply tank 21a or gas, such as external air, to a pipe line (not illustrated) within the ultrasonic endoscope 12.

First, the ultrasonic endoscope 12 illustrated in FIG. 1 has an ultrasonic observation part 36 and an endoscope observation part 38, which are constituted of the ultrasonic oscillator unit (46: refer to FIGS. 2 to 5) of the invention, at a distal end thereof, and images the inside of the body cavity of the subject to acquire the ultrasound image (echo signals) and the endoscopic image (image signals), respectively.

The ultrasonic endoscope 12 includes the ultrasonic observation part 36 and the endoscope observation part 38 at the distal end thereof, and is constituted of an insertion part 22 for being inserted into the body cavity of the subject, an operating part 24 that is installed consecutively with a proximal end part of the insertion part 22 to allow an operator, such as a doctor or an engineer to perform an operation, and a universal cord 26 has one end connected to the operating part 24.

An air/water supply button 28a that opens and closes an air/water supply pipe line (not illustrated) from the water supply tank 21a and a suction button 28b that open and close a suction pipe line (not illustrated) from the suction pump 21b are provided side by side at the operating part 24, and the operating part 24 is provided with a pair of angle knobs 29 and 29 and a treatment tool insertion port (also referred to as a forceps port) 30.

Here, the water supply tank 21a is a tank for storing the washing water to be supplied to the air/water supply pipe line within the ultrasonic endoscope 12 for washing the endoscope observation part 38 and the like of the ultrasonic endoscope 12. In addition, the air/water supply button 28a is used to jet gas, such as air, and water, such as washing water, which has been supplied through the air/water supply pipe line from the water supply tank 21a, from the endoscope observation part 38 on a distal end side of the insertion part 22.

Additionally, the suction pump 21b suctions the suction pipe line (not illustrated) in order to suction the suction object within the body cavity (including the supplied washing water) from the distal end side of the ultrasonic endoscope 12. The suction button 28b is used to suction the suction object within the body cavity from the distal end side of the insertion part 22 with a suction force of the suction pump 21b.

Additionally, the forceps port 30 is a port for allowing a treatment tool, such as forceps, a puncturing needle, or a high-frequency knife to be inserted therethrough.

The other end part of the universal cord 26 is provided with an ultrasonic wave connector 32a connected to the ultrasonic wave processor device 14, an endoscope connector 32b connected to the endoscope processor device 16, and a light source connector 32c connected to the light source device 18. The ultrasonic endoscope 12 is attachably and detachably connected to the ultrasonic wave processor device 14, the endoscope processor device 16, and the light source device 18 via the connectors 32a, 32b, and 32c, respectively. Additionally, an air/water supply tube 34a to which the water supply tank 21a is to be connected, a suction tube 34b to which the suction pump 21b is to be connected, and the like are connected to the light source connector 32c.

The insertion part 22 is constituted of the distal end part (distal end rigid part) 40 that is formed of a rigid member and has the ultrasonic observation part 36 and the endoscope observation part 38, a bending part 42 that is installed consecutively with a proximal end side of the distal end part 40, is formed by coupling a plurality of bendable pieces to each other, and is bendable, and a flexible part 43 that couples a proximal end side of the bending part 42 and a distal end side of the operating part 24 to each other and is thin, elongated, and flexible, sequentially from the distal end side.

The bending part 42 is remotely bending-operated by rotationally moving the pair of angle knobs 29 and 29 provided at the operating part 24. Accordingly, the distal end part 40 can be directed to a desired direction.

Additionally, a balloon into which an ultrasonic transmission medium (for example, water, oil, or the like) for covering the ultrasonic observation part 36 is injected may be attachably and detachably mounted on the distal end part 40. Since ultrasonic waves and the echo signals are significantly damped in the air, the ultrasonic transmission medium is injected into the balloon to expand the balloon and is made to abut against the region to be observed. Accordingly, air can be eliminated from between an ultrasonic oscillator (ultrasonic transducer) array (50: refer to FIGS. 2 to 5) of the ultrasonic observation part 36 and the region to be observed, and the damping of the ultrasonic waves and the echo signals can be prevented.

In addition, the ultrasonic wave processor device 14 is a device for creating and supplying ultrasonic signals (data) for generating the ultrasonic waves in the ultrasonic oscillator array (50: refer to FIGS. 2 to 5) of the ultrasonic oscillator unit (46) of the ultrasonic observation part 36 of the distal end part 40 of the insertion part 22 of the ultrasonic endoscope 12. Additionally, the ultrasonic wave processor device 14 is a device for receiving and acquiring the echo signals (data), which is reflected from the region to be observed to which the ultrasonic waves are radiated, with the ultrasonic oscillator array (50), and for creating the ultrasound image that is obtained by performed various kinds of signal (data) processing on the acquired echo signals and is displayed on the monitor 20.

The endoscope processor device 16 is a device for receiving and acquiring captured image signals (data) acquired from the region to be observed illuminated with the illumination light from the light source device 18 in the endoscope observation part 38 of the distal end part 40 of the insertion part 22 of the ultrasonic endoscope 12, and creating the endoscopic image that is obtained by performing various kinds of signal (data) processing and image processing on the acquired image signals and is displayed on the monitor 20.

In addition, the ultrasonic wave processor device 14 and the endoscope processor device 16 may be constituted of processors, such as a personal computer (PC).

In order to image the region to be observed within the body cavity to acquire the image signals with the endoscope observation part 38 of the ultrasonic endoscope 12, the light source device 18 is a device for generating illumination light, such as white light consisting of three primary color lights, such as red light (R), green light (G), and blue light (B), or specific wavelength light to supply the illumination light to the ultrasonic endoscope 12 to propagate the illumination light with a light guide or the like within the ultrasonic endoscope 12 (not illustrated), and emitting the illumination light from the endoscope observation part 38 of the distal end part 40 of the insertion part 22 of the ultrasonic endoscope 12 for illuminating the region to be observed within the body cavity with the illumination light.

The monitor 20 receives respective video signals created by the ultrasonic wave processor device 14 and the endoscope processor device 16 to display the ultrasound image and the endoscopic image. As for the display of the ultrasound image and the endoscopic image, it is possible to appropriately display one of the images on the monitor 20 through switching and to simultaneously display both the images. In addition, a monitor for displaying the ultrasound image and a monitor for displaying the endoscopic image may be separately provided, or the ultrasound image and the endoscopic image may be displayed in any other forms.

Next, the configuration of the distal end part of the insertion part of the ultrasonic endoscope will be described in detail with reference to FIGS. 2 to 4.

Figure 2:
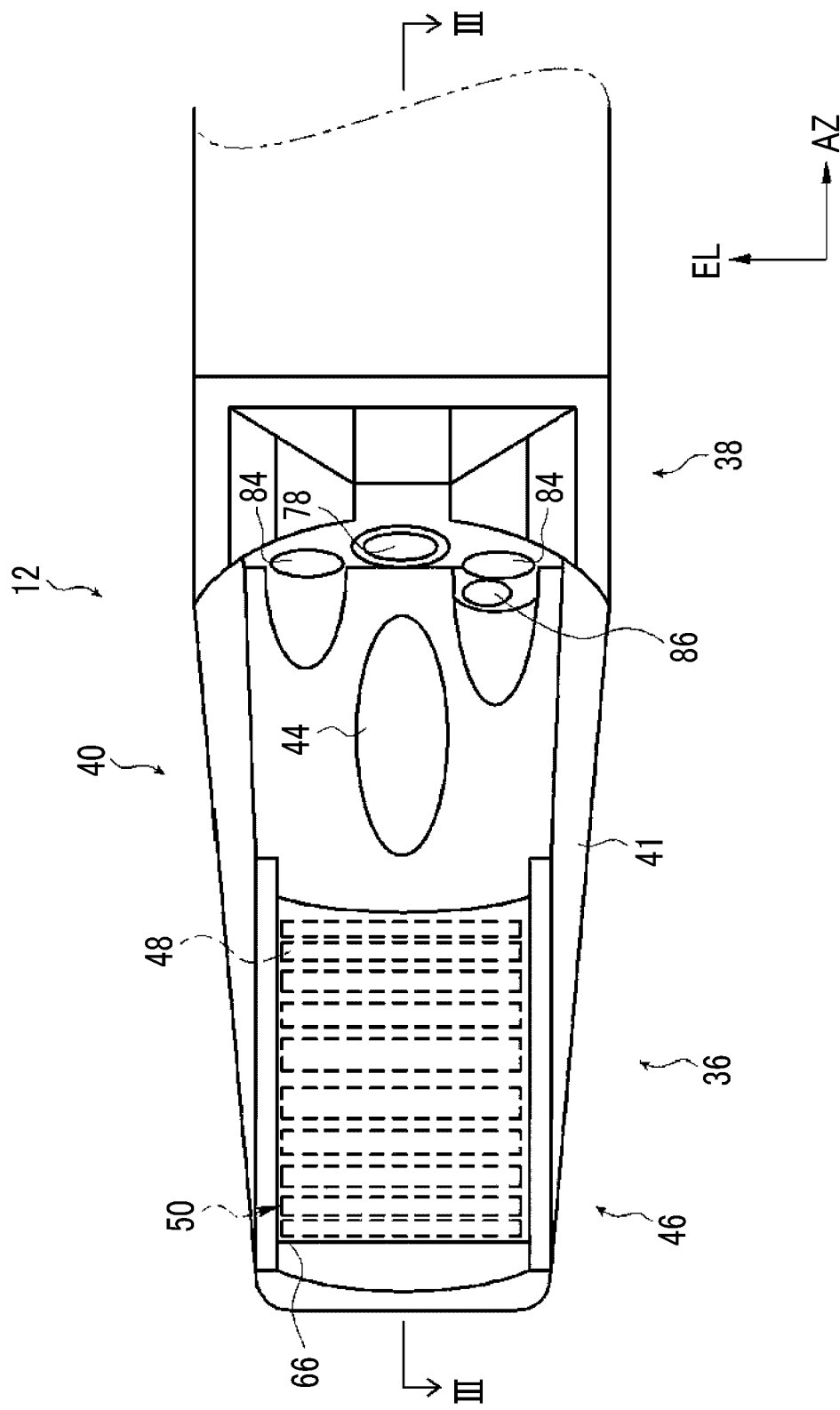
FIG. 2 is a partially enlarged plan view illustrating a distal end part of the ultrasonic endoscope illustrated in FIG. 1.

FIG. 2 is a partially enlarged plan view illustrating the distal end part of the ultrasonic endoscope illustrated in FIG. 1 and its vicinity. FIG. 3 is a view taken along line illustrated in FIG. 2 and seen from an arrow direction and is a longitudinal sectional view of the distal end part of the ultrasonic endoscope illustrated in FIG. 2 cut by a centerline in a longitudinal direction thereof. FIG. 4 is a partially enlarged longitudinal cross-sectional view of the ultrasonic observation part of the distal end part of the ultrasonic endoscope illustrated in FIG. 3, and is a view illustrating the configuration of the ultrasonic oscillator unit of the ultrasonic observation part. FIG. 5 is a view taken along line V-V illustrated in FIG. 3 and seen from an arrow direction and is a cross-sectional view cut by a centerline of a circular-arc structure of the ultrasonic oscillator array of the ultrasonic observation part of the distal end part of the ultrasonic endoscope illustrated in FIG. 3.

Figure 3:
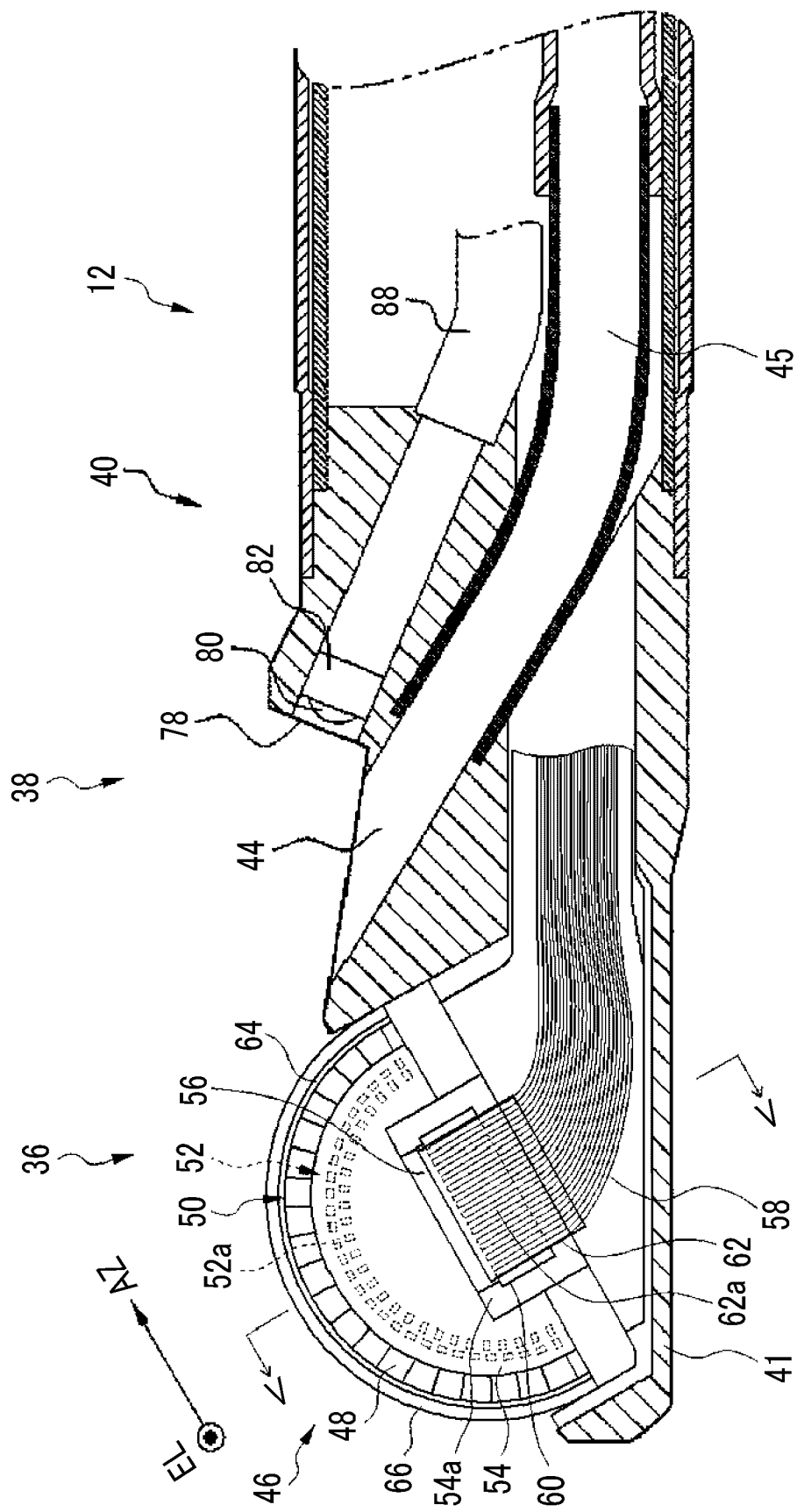
FIG. 3 is a view taken along line illustrated in FIG. 2 and seen from an arrow direction and is a partially longitudinal cross-sectional view of the distal end part of the ultrasonic endoscope illustrated in FIG. 2.

As illustrated in FIGS. 2 and 3, the distal end part 40 of the ultrasonic endoscope 12 is provided with the ultrasonic observation part 36 on a distal end side thereof for acquiring the ultrasound image, the endoscope observation part 38 on a proximal end side thereof for acquiring the endoscopic image, and a treatment tool delivery port 44 therebetween, and these are altogether attached to and held by a sheathing member 41 that serves as a distal end part body of the distal end part 40 of the ultrasonic endoscope 12 and is made of a rigid member, such as a hard resin.

In the example illustrated in FIG. 2, although the treatment tool delivery port 44 is provided between the ultrasonic observation part 36 and the endoscope observation part 38, the invention is not particularly limited to the illustrated example. The treatment tool delivery port 44 may be provided within the endoscope observation part 38 or may be provided closer to the proximal end side (bending part 42 side) than the endoscope observation part 38.

As illustrated in FIGS. 2 to 5, the ultrasonic observation part 36 is constituted of the ultrasonic oscillator unit 46 of the invention and the sheathing member 41 for attaching and holding the ultrasonic oscillator unit 46.

The ultrasonic oscillator unit 46 has the ultrasonic oscillator array 50 including a plurality of ultrasonic oscillators (transducers) 48, an electrode part 52 provided on an end surface of the ultrasonic oscillator array 50, a backing material layer 54 that supports the respective ultrasonic oscillators 48 of the ultrasonic oscillator array 50 from lower surface sides thereof in the drawing, a plurality of, that is, three or more, in the illustrated example, three flexible printed wired boards (hereinafter simply referred to as flexible printed circuits (FPCs)) 56 electrically connected to the electrode part 52 on one end side thereof, a plurality of, that is, three or more, in the illustrated example, three connectors 60 each having a mounting part 60a on which the other end of each FPC 56 is mounted, and a plurality of, that is, three or more, in the illustrated example, three cable wiring boards 62 that each have a cable wiring part 62a to which a plurality of cables 58 are wiring-connected and that are attached to the connectors 60, respectively.

In addition, in the present specification, the term "outside" means the outside of the distal end part 40 of the ultrasonic endoscope 12 or a side toward the outside, and the term "inside" means the inside of the distal end part 40 of the ultrasonic endoscope 12 or a side toward the inside. Additionally, in the present specification, the term "upper side" means, for example, an acoustic lens 66 side, more precisely, the ultrasonic oscillator array 50 side (to be described below), in the ultrasonic observation part 36 illustrated in FIGS. 3 to 5, and the term "lower side" means a sheathing member 41 side.

In the illustrated example, by individually mounting the other end sides of the three FPCs 56 on the mounting parts 60a of the three connectors 60, the FPCs 56 and the cable wiring boards 62 are electrically connected to each other by the connectors 60, and a plurality of individual electrodes 52a of the electrode part 52 provided on each outer side surface of the ultrasonic oscillator array 50 and the plurality of cables 58 are electrically connected to each other, respectively. In addition, the ultrasonic oscillator unit 46 may have a ground bar to which a plurality of common electrodes (for example, grounds (GNDs) 52b of the electrode part 52 are electrically connected, although not illustrated.

In the following, a case where each cable wiring board 62 is integrally attached to the connector 60, and a plurality of connection cores of the mounting part 60a of the connector 60 are electrically connected to the plurality of cables 58 that are wiring-connected to the cable wiring part 62a of the cable wiring board 62. However, the invention is not limited to this, and an end part (connecting terminals of wiring line) of each FPC 56 and an end part (connecting terminals of the cable wiring part 62a) of the cable wiring board 62 may be configured to be separately mounted on the connector 60.

Additionally, the ultrasonic oscillator unit 46 further has an acoustic matching layer 64 laminated on the ultrasonic oscillator array 50 and the acoustic lens 66 laminated on the acoustic matching layer 64. That is, the ultrasonic oscillator unit 46 includes a laminated body of the acoustic lens 66, the acoustic matching layer 64, the ultrasonic oscillator array 50, and the backing material layer 54.

The acoustic matching layer 64 is a layer for matching the acoustic impedance between a subject, such as a human body, and the ultrasonic oscillators 48.

The acoustic lens 66 attached on the acoustic matching layer 64 is a lens for condensing the ultrasonic waves emitted from the ultrasonic oscillator array 50 toward the region to be observed. The acoustic lens 66 is made of, for example, silicon-based resin (millable type silicone rubber (HTV rubber), liquid silicone rubber (RTV rubber), or the like), butadiene-based resin, polyurethane-based resin, or the like. In order for the acoustic matching layer 64 to match the acoustic impedance between the subject and the ultrasonic oscillators 48 and increase the transmittance of the ultrasonic waves, powder, such as titanium oxide, alumina, or silica, is mixed with the acoustic lens 66 as needed.

The ultrasonic oscillator array 50 is a 48-to-192 channel (CH) array including a plurality of, for example, 48 to 192 ultrasonic oscillators (transducers) 48 that are arranged outward in a convex circular-arc shape and have a rod shape, such as a rectangular parallelepiped shape.

That is, the ultrasonic oscillator array 50 is an array in which a plurality of ultrasonic oscillators 48 are arranged at a predetermined pitch in a one-dimensional array as in the illustrated example as an example, in a circular-arc shape with the longitudinal direction of the rod shape aligned. In this way, the respective ultrasonic oscillators 48 that constitute the ultrasonic oscillator array 50 are arranged at equal intervals in a convexly curved shape in an axis direction (the longitudinal axis direction of the insertion part 22) of the distal end part 40 and are sequentially driven on the basis of driving signals input from the ultrasonic wave processor device 14. Accordingly, convex electronic scanning is performed using a range where the ultrasonic oscillators 48 illustrated in FIG. 2 are arranged, as a scanning range.

The ultrasonic oscillator array 50 is arranged such that the length thereof in the width direction of the ultrasonic oscillator array 50 orthogonal to an AZ direction (AZ (azimuth) direction), that is, in a longitudinal direction (EL (elevation) direction) of the ultrasonic oscillators 48 is shorter than that in a direction parallel to a bottom surface 54*d* of the backing material layer 54 and a rear end side thereof is inclined so as to overhang. As illustrated in FIG. 5, each ultrasonic oscillators 48 has a configuration in which electrodes are formed on both surfaces of, for example, a thick film of a piezoelectric body, such as PZT (lead zirconium titanate) or PVDF (polyvinylidene fluoride). One electrode is an individual electrodes 52*a* that is separately independent for each ultrasonic oscillators 48, and the other electrode is a common electrode (for example, grand (touch-down) electrode) 52*b* common to all the ultrasonic oscillators 48. In the illustrated example, a plurality of the individual electrodes 52*a* extends lower surfaces of end parts of the plurality of ultrasonic oscillators 48 to an outer surface (top surface) 54*b* of the backing material layer 54 that serves as an arrangement surface, and the common electrode 52*b* is provided on upper surfaces of the end parts of the ultrasonic oscillators 48. The plurality of individual electrodes 52*a* and the common electrode 52*b* constitute the electrode part 52.

In addition, a gap between two adjacent ultrasonic oscillator 48 is filled with a filler material, such as epoxy resin.

In the ultrasonic oscillator unit 46 of the ultrasonic observation part 36, in a case where each ultrasonic oscillators 48 of the ultrasonic oscillator array 50 is driven and a voltage is applied to both the electrodes of the ultrasonic oscillators 48, the piezoelectric bodies oscillate to sequentially generate the ultrasonic waves, and the ultrasonic waves are radiated toward the region to be observed of the subject. Then, by sequentially driving the plurality of ultrasonic oscillators 48 with an electronic switch, such as a multiplexer, scanning is performed with the ultrasonic waves within a scanning range along a curved surface on which the ultrasonic oscillator array 50 is disposed, for example, within a range of about several tens of mm from the center of curvature of the curved surface.

Additionally, in a case where the echo signals (ultrasound echoes) reflected from the region to be observed are received, the piezoelectric bodies oscillate to generate voltages, and the voltages are output to the ultrasonic wave processor device 14 as electrical signals (ultrasonic detection signals) according to the received ultrasound echoes. After various kinds of signal processing are performed in the ultrasonic wave processor device 14, the ultrasound image is displayed on the monitor 20.

Figure 4:
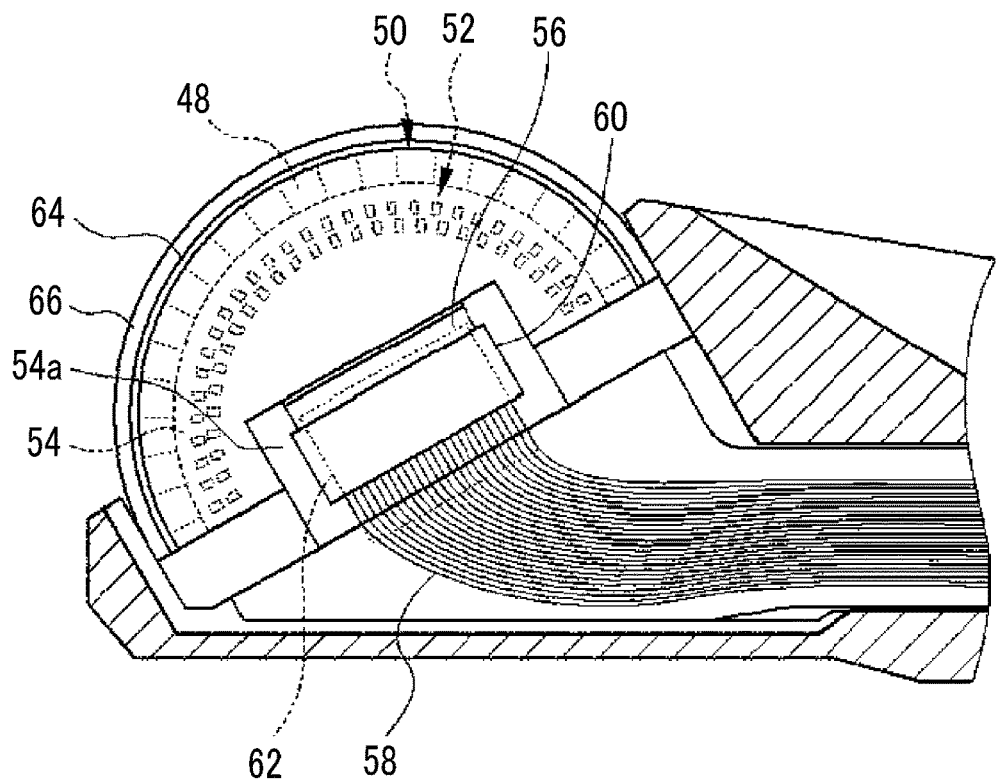
FIG. 4 is a partially enlarged cross-sectional view of an ultrasonic observation part of the distal end part of the ultrasonic endoscope illustrated in FIG. 2.
Figure 5:
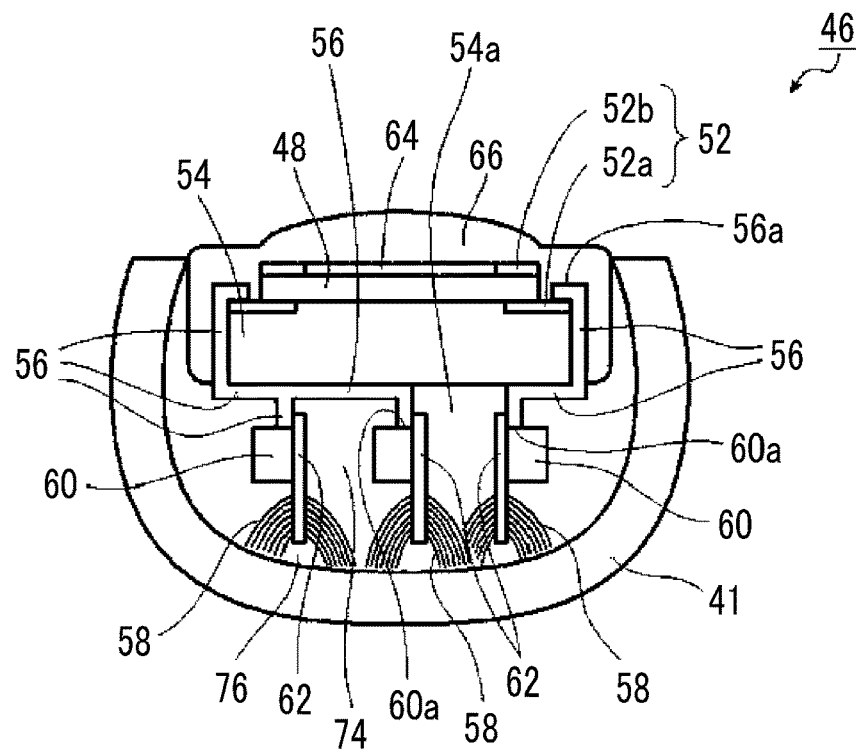
FIG. 5 is a view taken along line V-V illustrated in FIG. 3 and seen from an arrow direction and is a cross-sectional view of an example of the ultrasonic observation part of the distal end part of the ultrasonic endoscope illustrated in FIG. 3.

As illustrated in FIGS. 3 and 4, the electrode part 52 is provided in a circular-arc shape on an end surface side (of the respective ultrasonic oscillators 48) of the ultrasonic oscillator array 50 perpendicular to a circular-arc surface resulting from the arrangement of the plurality of (48 to 192) ultrasonic oscillators 48, that is, to the longitudinal direction of the rod shape of the ultrasonic oscillators 48, and includes the plurality of (48 to 192) electrodes 52*a* electrically connected to the plurality of (48 to 192) ultrasonic oscillators 48, respectively. In addition, the common electrode of the plurality of ultrasonic oscillators 48 may be included in the electrode part 52. In the invention, the "perpendicular" is not necessarily limited to 90 degrees, and includes perpendicular or substantially perpendicular, for example, 95 degrees±5 degrees, that is, an angle within a range of 85 degrees to 90 degrees.

In addition, in FIGS. 3 and 4, the plurality of electrodes 52*a* arranged in a circular-arc shape and the electrode part 52 including these electrodes are hidden under the backing material layer 54 and are not visible, but are indicated by dashed lines for easy understanding.

Although the electrode part 52 is provided on each outer side surface in the width direction of the ultrasonic oscillator array 50 perpendicular to the arrangement surface of the ultrasonic oscillators 48, that is, the longitudinal direction of the rod shape, that is, on at least one end surface of the ultrasonic oscillators 48, the electrode part 52 may be provided on an outer side surface on one side in a case where the number of ultrasonic oscillators 48 is small. Since it is preferable to the number of ultrasonic oscillators 48 is larger, it is preferable that the plurality of electrodes 52*a* are provided on both the outer side surfaces of the ultrasonic oscillator array 50. In addition, the plurality of electrodes 52*a* may be provided not on the outer side surfaces of the ultrasonic oscillator array 50 but on the center side thereof. In this way, even in a case the plurality of electrodes 52*a* are arranged in multiple rows, such as two rows, in the width direction of the ultrasonic oscillators 48, the plurality of electrodes 52*a* can be provided on the center side of the ultrasonic oscillator array 50. In this way, by providing the plurality of electrodes 52*a* on the center side of the ultrasonic oscillator array 50 in addition to both the outer side surfaces thereof, the number of ultrasonic oscillators 48, that is, the number of channels, can be increased.

In addition, in the example illustrated in FIG. 5, the plurality of electrodes 52*a* are constituted of the individual electrodes provided on the end surface sides of the respective ultrasonic oscillators 48 in their longitudinal direction. However, the invention is not limited to this. As long as the individual electrodes 52*a* of the ultrasonic oscillators 48 are electrically connected even in a case where the electrodes 52*a* are provided on any of one outer side surface, both outer side surfaces, and the center side of the ultrasonic oscillator array 50, the individual electrodes 52*a* may be constituted of separate electrodes connected by wiring lines from the individual electrodes. Additionally, although the common electrode is directly included in the electrode part 52, an electrode connected by a wiring line from the common electrode 52*b* may be included.

It is preferable that the plurality of electrodes 52*a* and the common electrode 52*b* of the electrode part 52 are provided as electrode pads.

Figure 6:
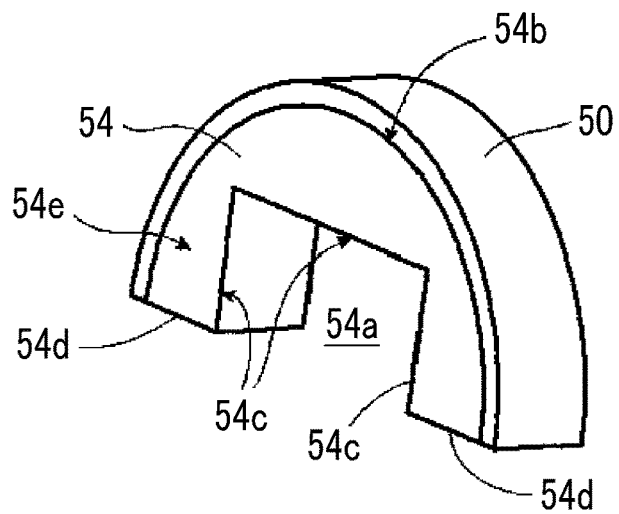
FIG. 6 is a perspective view illustrating an example of the structure of the backing material layer of the ultrasonic oscillator unit of the ultrasonic observation part illustrated in FIG. 4.

Next, as illustrated in FIGS. 3, 4, and 6, the backing material layer 54 is a layer of a member that is made of a backing material disposed on an inside with respect to the arrangement surface of the plurality of ultrasonic oscillators 48, that is, a rear surface (lower surface in the drawing) that becomes a center side of the circular-arc shape of the ultrasonic oscillator array 50. The backing material layer 54 has a top surface (an upper surface in the drawing) 54b formed in a convex circular-arc shape in cross-section and has an inner surface (a lower surface in the drawing) 54c formed in a concave circular-arc shape in cross-section, and accordingly, is made of a semicircular columnar backing material having the top surface 54b having the circular-arc cross-section and including a recess 54a on the inside opposite to the top surface 54b, preferably, a prismatic (rectangular parallelepiped-shaped) recess 54a penetrating from one outer side surface 54e of two outer side surfaces on both sides in the width direction of the backing material layer 54 to the other outer side surface 54e thereof in the illustrated example, that is, having the recess 54a having a rectangular cross-section on a lower surface side. Hence, in the illustrated example, the bottom surface 54d (inner surface) of the backing material layer 54 includes two separated planes that are located on the same plane as in the illustrated example.

Here, in the example illustrated in FIGS. 3, 4, and 6, the backing material layer 54 has a semicircular columnar shape having the recess 54a of which the inside is hollowed out in a prismatic shape. However, the invention is not limited to this. Any shapes may be adopted as long as the connectors 60 and the plurality of cables 58 connected to the connectors 60 can be housed inside a space between the bottom surface of the backing material layer and the sheathing member 41 or inside a space of the recess of the backing material layer, and a space between the bottom surface of the backing material layer and the sheathing member 41.

Figure 7:
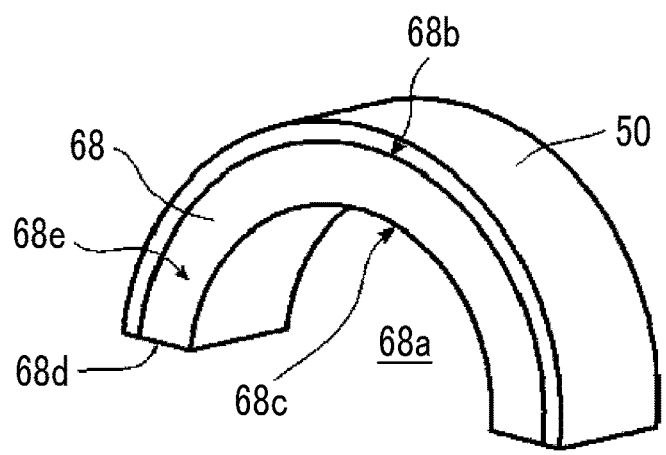
FIG. 7 is a perspective view illustrating a still further example of the structure of the backing material layer of the ultrasonic oscillator unit of the invention.
Figure 8:
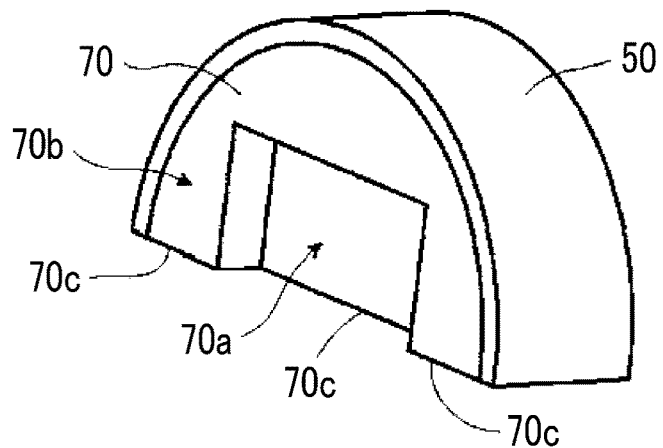
FIG. 8 is a perspective view illustrating a still further example of the structure of the backing material layer of the ultrasonic oscillator unit of the invention.
Figure 9:
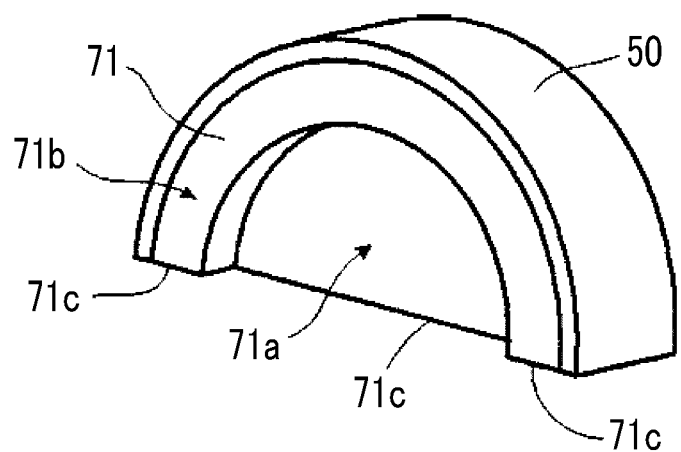
FIG. 9 is a perspective view illustrating a still further example of the structure of the backing material layer of the ultrasonic oscillator unit of the invention.
Figure 10:
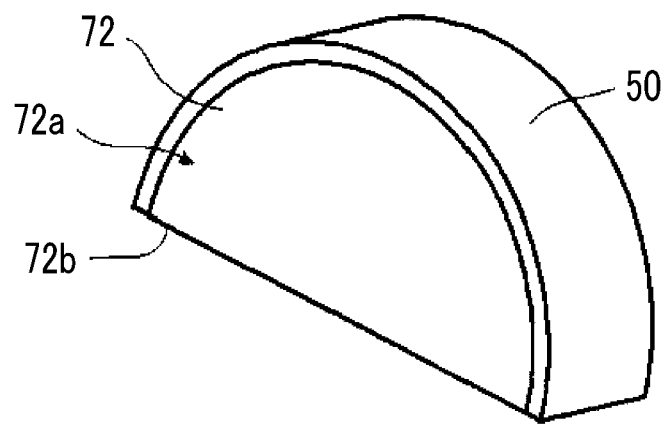
FIG. 10 is a perspective view illustrating a still further example of the structure of the backing material layer of the ultrasonic oscillator unit of the invention.

For example, a semicylindrical shape including a penetrating recess 68a having a semicircular columnar shape (a circular-arc cross-section) may be adopted as in the backing material layer 68 illustrated in FIG. 7, a semicircular columnar shape including a prismatic recess 70a that does not penetrate and a semicylindrical shape recess 71a that does not penetrate may be adopted as in backing material layers 70 and 71 illustrated in FIGS. 8 and 9, and a semicircular columnar shape that includes no recess may be adopted as in a backing material layer 72 illustrated in FIG. 10. In this case, it is preferable that a bottom surface 68d of the backing material layer 68 illustrated in FIG. 7 includes two separated planes that are located on the same plane, and it is preferable that all bottom surfaces 70c, 71c, and 72b of the backing material layers 70, 71, and 72 include one continuous plane located on the same plane.

In addition, in FIGS. 6 to 10, for the sake of description, constituent elements other than the ultrasonic oscillator array and the backing material layer among the constituent elements of the ultrasonic oscillator unit of the invention are omitted.

Moreover, the backing material layer used for the invention may have a semicircular columnar shape, may have a shape obtained by cutting a column with a plane parallel to a centerline, may have a semicircular columnar shape or a shape including a through recess having a cross-section, such as a polygonal shape, a semi-elliptical shape, or an abnormal shape, which opens from a bottom surface side of the backing material layer having a shape obtained by cutting the column with the plane parallel to the centerline and penetrates from one outer side surface of the backing material layer to the other outer side surface thereof, may have a semicylindrical shape, or may have a bow shape (a partial cylindrical shape with a circular arc smaller than a semicircle).

In addition, in the invention, each connector 60 has a rectangular shape in many cases. Thus, in that case, it is most preferable to use a semicircular columnar backing material layer having the recess 54a of which the inside is hollowed out in a prismatic shape as in the backing material layer 54 illustrated in FIGS. 3 and 6.

Additionally, it is preferable the backing material layer 54 of the illustrated example has the recess 54a that can include at least portions of the connectors 60. In the illustrated example, the recess 54a is a prismatic recess (first recess) penetrating from one outer side surface 54e of the backing material layer 54 to the other outer side surface 54e thereof. However, the invention is not limited to this, and any kind of recess may be adopted as long as the recess can house at least portions of the connectors 60.

For example, it is preferable that the recess of the backing material layer used for the invention is provided from the outer side surfaces of the backing material layer toward a center side of the backing material layer. Hence, it is more preferable that the recess is the recess (the first recess of the invention) penetrating from one outer side surface of the backing material layer to the other outer side surface thereof or a recess (a second recess of the invention) recessed from at least one outer side surface of the backing material layer toward the center side thereof.

Here, the first recess may be a recess (first recess) 68a that is circularly hollowed out from the bottom surface side of the backing material layer and penetrates from one outer surface 68e of the backing material layer 68 to the other outer surface 68e thereof, as illustrated in FIG. 7, as well as the prismatic recess 54a of the backing material layer 54 illustrated in FIG. 6, and may be a through recess, such as the above-described polygonal shape, semi-elliptical shape, or abnormal shape. The backing material layer 68 illustrated in FIG. 7 has a semicylindrical shape having a top surface 68b and a lower surface 68c having a circular-arc cross-section.

Meanwhile, the second recess may be a counterbore formed by performing counterboring from at least one outer side surface of the backing material layer toward the center side thereof, for example, a prismatic (quadrangular) counterbore 70a and a semicylindrical recess 71a respectively formed one-side outer side surfaces 70b and 71b of the semicircular columnar backing material layers 70 and 71 illustrated in FIGS. 8, and 9, a conical counterbore formed on one outer side surface of a semicircular columnar backing material layer, although not illustrated, or may be a bow-shaped counterbore, a polygonal counterbore, a pyramidal counterbore, or the like, although not illustrated. Additionally, even in a case where the recess is not above-described counterbore, a recess formed in advance in the backing material layer may be adopted as long as the recess is provided from the outer side surfaces of the backing material layer toward the center side thereof.

Moreover, it is preferable that such a recess is formed so as enlarge in a direction away from the ultrasonic oscillator array 50, for example, like the conical counterbore, as long as at least portions of the connectors 60 can be housed.

Moreover, in a case where recesses used in the invention do not penetrate like the counterbores (recesses) 70a and 71a, it is preferable that the recesses are provided on both the outer side surfaces, that is, both side surfaces of the backing material layer.

The backing material that constitutes the backing material layer 54 functions as a cushioning material that flexibly supports the respective ultrasonic oscillators 48 and the like of the ultrasonic oscillator array 50. For this reason, the backing material includes a material having rigidity, such as hard rubber, and an ultrasonic damping material (ferrite, ceramics, or the like) is added to the backing material as needed.

Hence, it is preferable that the ultrasonic oscillator array 50 is an array in which, in the illustrated example, the plurality of rectangular parallelepiped-shaped ultrasonic oscillators 48 are parallel to the longitudinal direction thereof, preferably, are arranged at equal intervals, on the circular-arc top surface 54*b* used as an upper surface of the backing material layer 54 formed in a circular-arc shape in cross-section, that is, an array in which the plurality of ultrasonic oscillators 48 are arranged outward in a circular-arc shape.

The FPC 56 is an electrode wiring board used after being mounted on the connector 60 as illustrated in FIGS. 3 and 4 in the invention, and has a plurality of wiring lines for being respectively electrically connected to the plurality of electrodes 52*a* of the electrode part 52. In the example illustrated in FIG. 5, three FPCs 56 are used after being mounted on three connectors 60.

Here, supposing the electrode part 52 has the plurality of, for example, 48 to 192 electrodes 52*a*, in the illustrated example, it is preferable that the three FPCs 56 each have a plurality of, for example, a predetermined number of (16 to 64) wiring lines for being respectively electrically connected to electrodes 52*a* of ⅓ of the number of electrodes of the plurality of electrodes 52*a*, for example, a predetermined number of (16 to 64) electrodes 52*a*. That is, in the illustrated example, it is preferable that one FPC 56 has a plurality of, for example, a predetermined number of (16 to 64) wiring pads 56*a* that are provided on one end side for being respectively electrically connected to a predetermined number of electrodes 52*a* (electrode pads) of the electrode part 52, a predetermined number of wiring lines (not illustrated) electrically connected to the predetermined number of wiring pads 56*a*, and a plurality of, for example, a predetermined number of (16 to 64) connecting terminals (not illustrated) that are provided on the other end side for being electrically connected to the predetermined number of wiring lines.

It is preferable that the end part of the other end side including the predetermined number of connecting terminals (not illustrated) of one FPC 56 is mounted on the mounting part 60*a* of one connectors 60 and is strongly fixed. Here, the predetermined number of (16 to 64) cables 58 are connected and fixed to the cable wiring board 62 attached to one connector 60, and the mounting part 60*a* of the connector 60 includes the plurality of, for example, a predetermined number of (16 to 64) connection cores (not illustrated) respectively electrically connected to the predetermined number of cables 58, and a GND part (not illustrated).

In this way, in the example illustrated in FIG. 5, the three FPC 56 are used after being mounted on the three connectors 60. Thus, it is preferable that in the mounting part 60*a*, one connector 60 is a connector having a plurality of cores having a predetermined number of connection cores, for example, a predetermined number of cores, such as 16 to 64 cores.

Here, the connectors 60 used for the invention are not particularly limited and may be any connectors as long as the connectors are capable of connecting the FPCs 56 and the cable wiring boards 62 to each other. For example, FPC connectors that connect end part electrodes of the FPCs to each other, board-to-FPC connecting connectors each including a socket and a header, and the like can be used. As the FPC connectors, for example, FVX connectors (made by a NIPPON PRESSURE TERMINAL MANUFACTURING CO. LTD.) having 0.2 mm pitch, and the like can be mentioned. Additionally, as the board-to-FPC connecting connectors, for example, narrow-pitch connectors F35S (made by PANASONIC ELECTRIC WORKS) having 0.35 mm pitch, and the like can be used.

In the invention, in a case where an FPC connector is used as each connector 60, the FPC 56 having an electrode at an end part thereof are used, the FPC connector is mounted and placed on each cable wiring board 62, and the end part electrode of FPC 56 is connected to the FPC connector (mounting part) mounted on the cable wiring board 62.

Meanwhile, in a case where a board-to-FPC connector is used as the connector 60, the socket is mounted on the FPC 56, the end part is connected to the socket, the header is mounted and placed on the cable wiring board 62, and the header mounted on the cable wiring board 62 is connected to the socket (mounting part) mounted on the FPC 56. In addition, in this case, on the contrary, the header may be mounted on the FPC 56, the socket may be mounted and placed on the cable wiring board 62, and both the header and the socket may be connected to each other.

In this way, the end part, for example, the end part electrode, the socket, or the header of one FPC 56 is mounted on and thereby integrated with the mounting part 60*a*, for example, a fitting part, the header, or the socket of one connector 60, and the predetermined number of connecting terminals (not illustrated) of the FPC 56 are brought into contact with and respectively electrically connected to the predetermined number of connection cores (not illustrated) of the mounting part 60*a* of the connectors 60, and thereby the predetermined number of electrodes 52*a* of the electrode part 52 and the predetermined number of cables 58 of the cable wiring board 62 on which the connector 60 is mounted are electrically connected to each other in one to one correspondence, respectively.

In addition, as in the example illustrated in FIG. 5, it is preferable that two connectors 60 among the three connectors 60 are respectively disposed in the longitudinal direction of the ultrasonic oscillators 48 on the two outer side surface 54*e* sides on both sides of the backing material layer 54 in the width direction thereof within the recess 54*a* of the backing material layer 54, and the one remaining connector 60 is disposed in the longitudinal direction of the ultrasonic oscillators 48 on a center side in the width direction between the two outer connectors 60.

In the illustrated example, the three FPCs 56 are attached to both end surfaces of the plurality of ultrasonic oscillators 48 by fixing the plurality of electrodes 52*a* of the electrode part 52 and the wiring pads 56*a* of the FPCs 56 in contact with each other, the two FPCs 56 of the three FPCs 56 extend along one outer side surface 54*e* of the backing material layer 54, the remaining one FPC 56 extends along the other outer side surface 54*e*, and both the two FPCs and the one remaining FPC are bent on the center side of the backing material layer 54 along the lower surface 54*c* in a case where the FPCs reach the recess 54*a*.

In a case where one of the two FPCs 56 extending along the lower surface 54*c* from one outer side surface 54*e* reaches the arrangement position of an outer connector 60 within the recess 54*a* of the backing material layer 54, the FPC is bent again and mounted on the mounting part 60*a* of the connector 60. The other one of the two FPCs 56 extends along the lower surface 54c on the center side within the recess 54a of the backing material layer 54, and is bent again and mounted on the mounting part 60a of the connector 60 in a case where the other FPC reaches the arrangement position of the connector 60 disposed on the center side. In a case where one of the two FPCs 56 extending along the lower surface 54c from the other outer side surface 54e reaches the arrangement position of an outer connector 60 within the recess 54a of the backing material layer 54, the FPC is bent again and mounted on the mounting part 60a of the connector 60.

In this way, the FPCs 56 are flexible wiring boards that are used after being bent in accordance with the shape of the backing material layer 54, particularly, the shape of the recess 54a. However, the invention is not limited to this. Any wiring boards may be adopted as long as the board can be electrically connected to the plurality of electrodes 52a of the electrode part 52 and can be mounted on the connectors 60 disposed in the width direction of the backing material layer 54 on the lower side of the backing material layer 54 or within the recess 54a. For example, rigid wiring boards, such as printed circuit boards (hereinafter referred to as printed circuit boards (PCBs)) or printed wired boards (hereinafter referred to as printed wired boards (PWBs), having the bent shape as illustrated in FIG. 5, may be used, or for example, multilayer boards each obtained by integrating a flexible wiring board, such as the FPC 56, and a rigid wiring board with each other is used.

Meanwhile, in a case where the FPCs 56 are attached to the electrode part 52 of the ultrasonic oscillator array 50, it is preferable to electrically connect the plurality of wiring pads 56a and the plurality of electrodes 52a (electrode pads) to each other by pasting the ultrasonic oscillator array 50 and the FPCs 56 to each other such that the plurality of wiring pads 56a of the FPCs 56 and the plurality of electrodes 52a (electrode pads) of the electrode part 52 of the ultrasonic oscillator array 50 come into contact with each other.

Here, the electrical connection between the plurality of wiring pads 56a of the FPCs 56 and the plurality of electrodes 52a (electrode pads) of the electrode part 52 of the ultrasonic oscillator array 50 is preferably performed by soldering. However, the electrical connection may be performed by interposing wiring electrodes of the end parts of the FPCs 56 below the ultrasonic oscillators 48 and using a conductive adhesive. In addition, the electrical connection between the wiring pads 56a and the electrodes 52a is not necessarily limited to these connection methods, and any methods may be used as long as the workability of wiring is not hindered and the difficulty of an operation step does not become high, or well-known methods, such as a method of performing pasting using an anisotropic conductive sheet or anisotropic conductive paste, a method, such as wire bonding, and a method using heat fusion, may be used.

In the invention, the number of channels are divided into three or more groups in accordance with the number of the plurality of electrodes 52a of the electrode part 52 of the ultrasonic oscillator array 50, that is, the number of channels, and the number of connection cores of the connectors 60 having a size that can be applied to the size of the ultrasonic oscillator array 50 of the ultrasonic observation part 36 of the ultrasonic endoscope 12, and three or more, in the example illustrated in FIG. 5, three FPCs 56 each having wiring pads 56a equal to or more than the number of channels of each group, and three or more, in the example illustrated in FIG. 5, three connectors 60 each having connection cores equal to or more than the number of channels of each group are used.

That is, as the connectors, there are prepared three or more connectors 60 in which the plurality of cables 58 are divided into a predetermined number of (three or more) groups equal to or more than the number of channels of each group, the predetermined number of cables 58 of each group are wiring-connected to the cable wiring parts 62a of the cable wiring boards 62 in advance, the cable wiring boards 62 to which the predetermined number of cables 58 are wiring-connected are respectively attached to the connectors 60, the predetermined number of cables 58 and the predetermined number of connection cores of the mounting part 60a are electrically connected to each other, and the predetermined number of cables 58 are respectively electrically connected thereto.

In addition, the method of wiring-connecting the plurality of cables 58 to the cable wiring parts 62a of the cable wiring boards 62 and the method of electrically the connection cores of the cable wiring parts 62a and the mounting part 60a are not also particularly limited. Similarly to the method of electrical connection between the wiring pads 56a of the FPCs 56 and the electrodes 52a of the electrode part 52, the well-known methods, such as the method using soldering, the method using an anisotropic conductive sheet or anisotropic conductive paste, the method, such wire bonding, or the method using heat fusion, can be used.

Additionally, the cable wiring boards 62 used for the invention are not particularly limited, and may be the rigid wiring boards, such as the PCBs or the PWBs, the flexible wiring boards, such as the FPCs, and the multilayer boards each obtained by integrating a flexible wiring board and a rigid wiring board with each other.

Meanwhile, as the FPCs, there are prepared three or more the FPCs 56 in which the plurality of electrodes 52a of the electrode part 52 of the ultrasonic oscillator array 50 are divided into three or more groups having a predetermined number of (3 or more) channels equal to or more than the number of channels of each group, and the electrodes 52a having the predetermined number of channels of each group are connected to the respective FPCs 56 in advance, and the electrodes 52a having the predetermined number of channels are electrically connected thereto, respectively.

In this way, the plurality of electrodes 52a of the electrode part 52 and the plurality of cables 58 can be easily electrically connected to each other by mounting the respective end parts of the three FPCs 56 respectively electrically connected to the predetermined number of electrodes 52a of the electrode part 52 of the ultrasonic oscillator array 50 in advance on the mounting parts 60a of the three or more connectors 60 to which the predetermined number of cables 58 are respectively electrically connected via the cable wiring boards 62 in advance, in one to one correspondence.

Additionally, although described below, the heat dissipation effect from a central part of the backing material layer 54 can be expected by disposing a third FPC 56 at the center of the ultrasonic oscillator array 50 in addition to a heat dissipation path through the filler layers 74 and 76 from the sheathing member (case) 41 resulting from disposing the two FPCs 56 on both the outer side of the ultrasonic oscillator array 50.

As described above, in the invention, it is possible to provide the ultrasonic oscillator unit that can simplify ultrasonic oscillator wiring task, improve efficiency and improve workability, can be small-sized, has excellent workability in a case where the respective electrodes of the ultrasonic oscillator array and numerous cables are wired and low difficulty of the operation step, has a wiring structure in which a load on a cable is unlikely to occur and there is less risk of disconnection, allows further improvement in the heat dissipation effect from the ultrasonic oscillator array generating heat to be expected, and is suitable for use in the ultrasonic endoscope.

Moreover, in the invention, it is possible to provide the ultrasonic oscillator unit that is capable of inspecting the ultrasonic oscillator array before cable wiring, has high manufacture stability, and does not cause an increase in cost, and is suitable for use in the ultrasonic endoscope.

In addition, in the invention, the connectors are not particularly limited, and any connectors may be adopted as long as the connectors can electrically connect the predetermined number of cables 58 to the predetermined number of electrodes 52a of the electrode part 52 in a case where the end part of each FPC 56 is mounted on the mounting part 60a and have a size and the number of connection cores (the number of channels) required for the ultrasonic oscillator unit 46 of the ultrasonic observation part 36 of the ultrasonic endoscope 12. However, it is necessary to use at least three or more connectors 60. Hence, it is preferable that the connectors 60 are connectors in which the size is as small as possible and the number of connection cores is larger. However, in order to make the sensitivity of the ultrasonic oscillator unit 46 high, it is necessary to apply a high voltage to the ultrasonic oscillators 48 to send a large electric current thereto, and it is also necessary that the number of connection cores and the size of wiring lines are more than certain values. Therefore, the connectors 60 may be selected in accordance with the size of the ultrasonic oscillator unit 46, the number of connection cores, the size of connection cores and wiring lines, and the like. As the connectors used for the invention, for example, connectors having a connector length of 9.4 mm and 40 cores, connectors having a connector length of 9.0 mm and 35 cores, and the like can be mentioned.

In this way, in the invention, three or more wiring boards, such as the FPCs, the PCBs, or the PWBs, can be disposed within the ultrasonic endoscope 12 by using the connectors having short connector lengths.

In the invention, it is necessary to use the three or more connectors and the three or more FPCs. This is because it is difficult to obtain a required number of channels and required sensitivity as described above with two or less connectors and two or less FPCs. Additionally, although described below, this is because the heat dissipation path from the ultrasonic oscillator array 50 of the ultrasonic oscillator unit 46 to be limited to a heat dissipation path to the sheathing member (case) 41 via the two or less FPCs and the filler layers 74 and 76, a sufficient heat dissipation path cannot be secured, and it is difficult to obtain high-sensitivity.

In the invention, the connectors 60 need to be housed on the lower side of the backing material layer 54, that the rear surface side of the backing material layer 54 opposite to the ultrasonic oscillator array 50, and accordingly, between housed between the bottom surface 54d of the backing material layer 54, and the sheathing member 41. However, it is preferable that at least portions of the connectors 60 are included in the recess 54a of the backing material layer 54. That is, it is preferable that the recess 54a is a space that can house at least portions of the connectors 60. In addition, in the ultrasonic oscillator unit 46 of the invention, as illustrated in FIGS. 3, 4, and 5, most of each of the three connectors 60 are housed in a semicircular columnar recess 54a.

In this way, by housing respective portions of the three connectors 60, to which the predetermined number of cables 58 are respectively wiring-connected, in the recess 54a of the backing material layer 54, the three connectors 60, the three cable wiring boards 62, and the plurality of cables 58 can be reliably disposed between the recess 54a of the backing material layer 54, and the sheathing member 41, and the space within the ultrasonic observation part 36 of the distal end part 40 of the ultrasonic endoscope 12 can be effectively used in the invention. As a result, size reduction of the ultrasonic oscillator unit 46 and eventually size reduction of the ultrasonic endoscope 12 can be achieved.

Here, in the ultrasonic oscillator unit 46 of the invention, as illustrated in FIG. 5, it is preferable that a gap of the recess 54a between the three connectors 60, the three cable wiring boards 62, and the plurality of cables 58 that are housed in the semicircular columnar recess 54a of the backing material layer 54, and the backing material layer 54, that is, a space, which is not occupied by portions of the three connectors 60, the three cable wiring boards 62, and the plurality of cables 58 within the recess 54a of the backing material layer 54, is filled with a filler and is used as a filler layer 74.

In addition, in a case where the ultrasonic oscillator unit 46 of the invention is attached to the sheathing member 41 of the distal end part 40 of the ultrasonic endoscope 12, it is preferable that a gap (space) between the ultrasonic oscillator unit 46, that is, the acoustic lens 66, the FPCs 56, the filler layer 74, and the remaining portions of the three connectors 60, the three cable wiring boards 62, and the plurality of cables 58, and the sheathing members 41, is filled with a filler having excellent heat dissipation and is used as a filler layer 76.

Such filler layers 74 and 76 are provided in order to fill the gap within the recess 54a of the backing material layer 54, and the gap between the ultrasonic oscillator unit 46 and the sheathing member 41, and can fix portions of the three connectors 60, the three cable wiring boards 62, and the plurality of cables 58 to prevent disconnection of the cables 58 and the like. In this way, by covering at least portions of the three connectors 60, the three cable wiring boards 62, and the plurality of cables 58 with the filler and forming the filler layers 74 and/or 76, the portions of the plurality of cables 58 during handling of an assembly of the ultrasonic oscillator unit 46 of the invention and the ultrasonic observation part 36 can be protected.

Moreover, it is preferable that the acoustic impedances of the filler layer 74 and the backing material layer 54 are matched with each other such that the ultrasonic waves, which are oscillated from the ultrasonic oscillator array 50 and propagated to a lower side thereof, are not reflected at a boundary between the filler layer 74 and the backing material layer 54 and such that the ultrasonic waves oscillated from the ultrasonic oscillator array 50 can be reflected in an observation target or its peripheral part and can sufficiently damp the ultrasonic waves propagated to the lower side of the ultrasonic oscillator array 50. For that reason, in a case where the acoustic impedance of the filler layer 74 is defined as Zp and the acoustic impedance of the backing material layer 54 is defined as Zb, it is preferable that an acoustic impedance reflectivity Q of the filler layer 74 and the backing material layer 54 expressed by the following Equation (1) is 50% or less.

$$Q=100\times|Zp-Zb|/(Zp+Zb) \qquad (1)$$

Here, the unit of the acoustic impedance Zp and Zb is $kg/(m^2 \cdot s)$. In addition, kg represents kilogram, m represents meter and s represents second.

The acoustic impedance reflectivity is an index showing the easiness of reflection of the ultrasonic waves (acoustic beams) on a boundary surface between the filler layer 74 and the backing material layer 54, that is, shows that the acoustic impedance of the filler layer 74 and the acoustic impedance of the backing material layer 54 are matched with each other as the value thereof is closer to 0%. In a case where the above acoustic impedance reflectivity is about 50% or less, the noise caused by the ultrasonic waves propagated to the lower side of the ultrasonic oscillator array 50 can be processed so as not to become a problem in creating the ultrasound image in the ultrasonic wave processor device 14 using the ultrasonic signals received in the ultrasonic oscillator array 50.

In addition, also in the filler layer 76, it is more preferable to take the matching of the acoustic impedance with the backing material layer 54, similarly to the filler layer 74.

Additionally, in a case where the ultrasonic waves are oscillated from the ultrasonic oscillator array 50 of the ultrasonic oscillator unit 46, the driving signals transmitted from the ultrasonic wave processor device 14 to the ultrasonic oscillator array 50 become thermal energy and the ultrasonic oscillator array 50 generates heat. Therefore, it is preferable that the filler layer 76 has heat dissipation. For that reason, it is preferable that the thermal conductivity of the filler layer 76 is 1.0 W/m·K or more. Here, W represents watt, m represents meter and K represents Kelvin.

In addition, also in the filler layer 74, it is more preferable to use the filler having excellent heat dissipation similarly to the filler layer 76.

In this way, not only the heat generated in the ultrasonic oscillator array 50 can be dissipated to the sheathing member 41 through the filler layers 74 and 76 via the two FPCs 56, the two connectors 60, and two cable wiring boards 62 on both outer sides of the backing material layer 54 in the width direction thereof and can be dissipated from the two cable wiring boards 62 to the plurality of cables 58, but also the heat can be dissipated to the sheathing member 41 through the filler layers 74 and 76 via the one FPC 56, the one connector 60 and the one cable wiring board 62 on the center side in a center region in the width direction of the backing material layer 54 and can be dissipated from the one cable wiring board 62 to the plurality of cables 58.

In this way, in the invention, since the heat dissipation path via the backing material layer 54 on the central side of the backing material layer 54 in the width direction can be increased in addition to the heat dissipation paths on both the outer sides of the backing material layer 54 in the width direction thereof, the heat dissipation of the ultrasonic oscillators 48 of the ultrasonic oscillator array 50 can be promoted, and a temperature rise on the surface of the ultrasonic oscillators 48 and the acoustic lens 66 can be suppressed. As a result, the upper limit of the output of the ultrasonic oscillators 48 specified to the temperature rise value of the surface of the acoustic lens 66 can be raised, the output of the ultrasonic oscillator unit 46 can be improved, and high output can be obtained.

Here, in the ultrasonic oscillator unit 46 illustrated in FIG. 5, it is preferable that the portions of at least of the wiring pads 56a of the FPCs 56 extend and are pasted onto the electrodes 52a of the electrode part 52 of the ultrasonic oscillator array 50 disposed on the top surface the backing material layer 54 that is the arrangement surface of the ultrasonic oscillators 48, both are bonded together using the anisotropic conductive sheet or the anisotropic conductive paste or by the heat fusion, and both are electrically connected to each other. However, it is needless to say that the invention is not limited to this.

Figure 11:
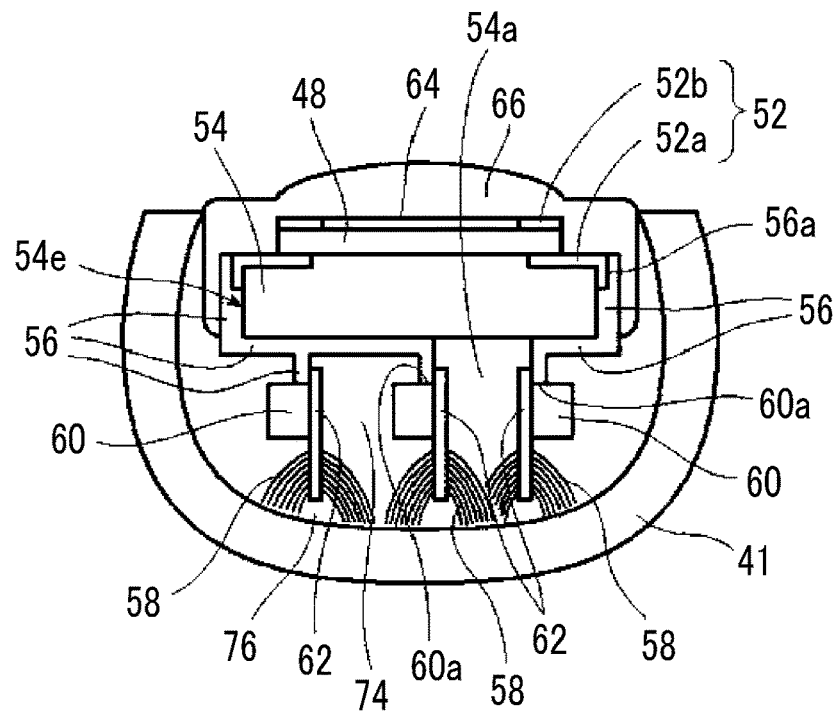
FIG. 11 is a cross-sectional view of still another example of the ultrasonic observation part of the distal end part of the ultrasonic endoscope of the invention.

For example, as illustrated in FIG. 11, the electrodes 52a of the electrode part 52 of the ultrasonic oscillator array 50 may be made to extend from the top surface 54b (the arrangement surface of the ultrasonic oscillators 48) of the backing material layer 54 to an outer side surface 54e, the thickness of portions of at least the wiring pads 56a of the FPC 56 may be made smaller by that amount, and the extending portions of the electrodes 52a extending to the outer side surface 54e of the backing material layer 54 and the portions of the wiring pads 56a of the FPC 56 of which the thickness is made smaller are pasted and joined to each other and both may be electrically connected to each other solder or the like.

Figure 12:
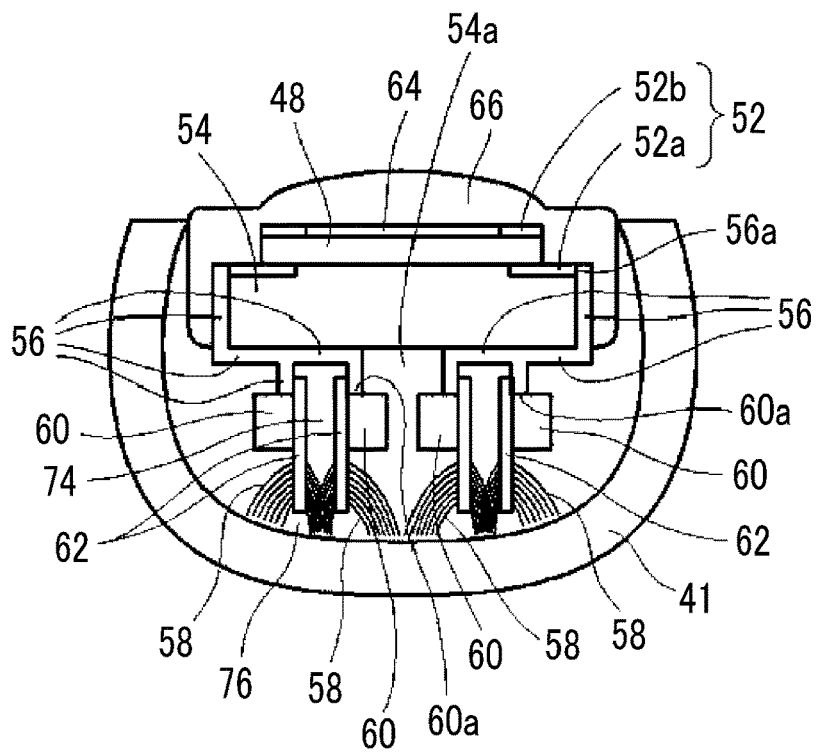
FIG. 12 is a cross-sectional view of still another example of the ultrasonic observation part of the distal end part of the ultrasonic endoscope of the invention.

Additionally, in the example illustrated in FIG. 12, the electrical connection between the FPCs 56 (wiring pads 56a) and the electrodes 52a of the electrode part 52 of the ultrasonic oscillator array 50 may be performed by pasting and joining the wiring pads 56a of side surfaces of distal end portions of the FPCs 56 and the electrodes 52a of the electrode part 52 of the outer side surface (end surfaces of the ultrasonic oscillators 48) of the ultrasonic oscillator array 50 to each other, similarly to the above-described example and by electrically connecting both the FPCs 56 (wiring pads 56a) and the electrodes 52a of the electrode part 52 of the ultrasonic oscillator array 50.

In addition, four FPCs 56, four able wiring boards 62, and four connectors 60 are used in the example illustrated in FIG. 12. However, the invention is not limited to this. As long as three or more FPCs 56, three or more cable wiring boards 62, and three or more connectors 60 are used, several FPCs, several cable wiring boards, several connectors may be used.

Additionally, in the example illustrated in FIGS. 11 and 12, the backing material layer 68 having the prismatic (recess) 54a illustrated in FIG. 6 is used similarly to the example illustrated in FIG. 5. However, the invention is not limited to this. The semicylindrical backing material layer 54 having the penetrating semicircular columnar recess 68a illustrated in FIG. 7 may be used, the backing material layers 70 and 71 that respectively have the non-penetrating prismatic counterbore (recess) 70a and the non-penetrating semicircular columnar counterbore (recess) 71a, as illustrated in FIGS. 8 and 9, may be used, the backing material layer 72 with no counterbore (recess) as illustrated in FIG. 10 may be used, or backing material layers having other shapes and structures may be used.

The endoscope observation part 38 is constituted of an observation window 78, an objective lens 80, a solid-state imaging element 82, an illumination window 84, a washing nozzle 86, a wiring cable 88, and the like.

The distal end part 40 is detached obliquely upward of the observation window 78. The reflected light of the region to be observed, which has been incident from the observation window 78, is focused on an imaging surface of the solid-state imaging element 82 by the objective lens 80. The solid-state imaging element 82 photoelectrically converts of the reflected light of the region to be observed transmitted through the observation window 78 and the objective lens 80 and focused on the imaging surface, and outputs imaging signals. As the solid-state imaging element 82, a charge-coupled device (CCD), a complementary metal oxide semiconductor (CMOS), or the like can be used. The captured image signals output by the solid-state imaging element 82 are transmitted to the endoscope processor device 16 by the universal cord 26 via the wiring cable 88 extending from the insertion part 22 to the operating part 24. The endoscope processor device 16 performs various kinds of signal processing and image processing with respect to the transmitted imaging signals, and displays the processed signals as the endoscopic optical image on the monitor 20.

Illumination windows 84 are provided on both sides with the observation window 78 interposed therebetween. An exit end of the light guide (not illustrated) is connected to the illumination windows 84. The light guide is provided to extend from the insertion part 22 to the operating part 24 and has an incident end connected to the light source device 18 connected via the universal cord 26. The illumination light emitted by the light source device 18 is transmitted to the light guide and is radiated from the illumination windows 84 to a region to be observed.

Additionally, the washing nozzle 86 jets air or washing water toward the observation window 78 and the illumination windows 84 through the air/water supply pipe line within the ultrasonic endoscope 12 from the water supply tank 21a in order to clean the surfaces of the observation window 78 and the illumination windows 84.

Additionally, the distal end part 40 is provided with the treatment tool delivery port 44. The treatment tool delivery port 44 is connected to a treatment tool channel 45 to be inserted through the inside of the insertion part 22, and a treatment tool inserted into a forceps port 30 serving as a treatment tool insertion port is introduced into the body cavity via the treatment tool channel 45 from the treatment tool delivery port 44. In addition, although the treatment tool delivery port 44 is located between the ultrasonic observation part 36 and the endoscope observation part 38, it is preferable to dispose the treatment tool delivery port 44 close to the ultrasonic observation part 36 in a case where the movement of the treatment tool introduced into the body cavity from the treatment tool delivery port 44 is confirmed with the ultrasound image.

Although not illustrated, a rising stand that changes a delivery direction of the treatment tool introduced into the body cavity from the treatment tool delivery port 44 may be provided inside the treatment tool delivery port 44. A wire (not illustrated) is attached to the rising stand, the standing angle of the rising stand is changed by a push/pull operation resulting from the operation of a standing lever (not illustrated) of the operating part 24, and thereby the treatment tool is delivered in a desired direction.

In a case where the inside of the body cavity is observed by the ultrasonic endoscope 12, first, the insertion part 22 is inserted into the body cavity and searches for the region to be observed while the endoscopic optical image acquired in the endoscope observation part 38 is observed by the monitor 20.

Next, in a case where the distal end part 40 reaches the region to be observed and an instruction for acquiring the ultrasonic tomographic image is made, a driving control signal is input from the ultrasonic wave processor device 14 via the cables 58, the three or more cable wiring boards, the three or more connectors 62, the three or more FPCs 56, and the electrode part 52 within the ultrasonic endoscope 12, to the ultrasonic oscillators 48. In a case where the driving control signal is input, a regular voltage is applied to both the electrodes of each ultrasonic oscillators 48. Then, the piezo-electric bodies of the ultrasonic oscillators 48 are excited, and the ultrasonic waves are emitted to the region to be observed via the acoustic lens 66.

The echo signals from the region to be observed are received by the ultrasonic oscillators 48 after the radiation of the ultrasonic waves. The radiation of the ultrasonic waves and the reception of the echo signals are repeatedly performed while the ultrasonic oscillators 48 to be driven are shifted by the electronic switch, such as the multiplexer. Accordingly, the region to be observed is scanned with the ultrasonic waves. In the ultrasonic wave processor device 14, the ultrasonic tomographic image is created on the basis of the detection signals output from the ultrasonic oscillators 48 upon receiving the echo signals. The created ultrasonic tomographic image is displayed on the monitor 20.

In the invention, the connectors 60 are used. However, in a case where the backing material layer 72 as illustrated in FIG. 10 is used, in the case of such a size that the connectors 60 is not accommodated in a space between the backing material layer 72 and the case (sheathing member 41), it is preferable to dispose the connectors 60 even in the recesses 54a, 68a, 70a, 71a within the backing material layers 54, 68, 70, and 71, using the backing material layers 54, 68, 70, and 71 illustrated in FIGS. 6 to 9.

However, in this case, in a case where the connectors the disposed below the backing material of the ultrasonic oscillator at the end parts, there is a concern about influence on ultrasonic oscillator characteristics.

For this reason, by reducing the number of connection cores per one connector, that is, the number of wiring lines per one cable wiring board, a connector size in the azimuth (AZ) direction (refer to FIG. 3) can be made small, and it is possible to reduce influence of the characteristics to end part elements in a case where elements are disposed within a backing material, for example, in a recess within a backing material layer. In this way, by reducing the number of channels per one connector.

In this way, by reducing the number of channels per one connector, connector length can be shortened and the elements can be arranged within the backing material layer.

In addition, in the related-art structures, the number of cable wiring lines per one cable wiring board, such as a PCB, increased, and a wiring structure around a cable soldered part is complicated. However, in the invention, any interference between the cables of the distal end part of the ultrasonic endoscope can be avoided by dividing the space of the wiring part by the cable wiring boards, such as the PCBs.

Basically, the ultrasonic oscillator unit of the invention is configured as described above.

Although the ultrasonic oscillator unit related to the invention have been described above in detail, it is natural that the invention is not limited to the above examples, and various improvements and modifications may be made without departing from the scope of the invention.

EXPLANATION OF REFERENCES

10: ultrasonic inspection system
12: ultrasonic endoscope
14: ultrasonic wave processor device
16: endoscope processor device
18: light source device
20: monitor
21a: water supply tank
21b: suction pump
22: insertion part
24: operating part
26: universal cord
28a: air/water supply button
28b: suction button
29: angle knob
29, 30: treatment tool insertion port (forceps port)
32a: ultrasonic wave connector
32b: endoscope connector 32c: light source connector
34a: air/water supply tube
34b: suction tube
36: ultrasonic observation part
38: endoscope observation part
40: distal end part
41: sheathing member
42: bending part
43: flexible part
44: treatment tool insertion port
46: ultrasonic oscillator unit
48: ultrasonic oscillator
50: ultrasonic oscillator array
52: electrode part
52a: individual electrode
52b: common electrode
54, 68, 70, 71, 72: backing material layer
54a, 68a, 70a, 71a: recess
54b, 68b: outer surface (top surface)
54c, 68c: lower surface
54d, 68d, 70c, 71c, 72b: bottom surface (inner surface)
54e, 68e, 70b, 71b, 72a: outer side surface
56: flexible printed wired board (FPC)
56a, 56b: wiring pad
58: cable
60: connector
60a: mounting part
62: cable wiring board
62a: cable wiring part
64: acoustic matching layer
66: acoustic lens
74, 76: filler material layer
78: observation part
80: objective lens
82: solid-state imaging element
84: illumination window
86: washing nozzle
88: wiring cable
EL: longitudinal direction (elevation direction)
AZ: parallel direction (azimuth direction)

What is claimed is:

1. An ultrasonic oscillator unit comprising:
an ultrasonic oscillator array in which a plurality of ultrasonic oscillators having a rod shape are arranged in a circular-arc shape while aligning in a longitudinal direction of the rod shape;
an electrode part that is provided in at least one end surface of the plurality of ultrasonic oscillators perpendicular to the longitudinal direction and has a plurality of electrodes electrically connected to the plurality of ultrasonic oscillators, respectively;
a circular-arc backing material layer disposed on a rear surface of the ultrasonic oscillator array that becomes a center side of the circular-arc shape;
three or more electrode wiring boards electrically connected to the plurality of electrodes of the electrode part; and
three or more connectors to which a plurality of cables are connected, respectively,
wherein the three or more electrode wiring boards are respectively mounted to the three or more connectors and electrically connect the plurality of electrodes of the electrode part to the plurality of cables, and
wherein the three or more connectors are arranged in a width direction of the circular-arc backing material layer in the longitudinal direction on a rear surface side of the circular-arc backing material layer opposite to the ultrasonic oscillator array.

2. The ultrasonic oscillator unit according to claim 1, wherein the three or more electrode wiring boards are flexible printed wired boards or rigid printed wiring boards.

3. The ultrasonic oscillator unit according to claim 1, wherein the three or more electrode wiring boards are electrically connected to the electrode part via heat fusion connection, and are disposed on outer side surface, in the width direction, of the ultrasonic oscillator array in the longitudinal direction.

4. The ultrasonic oscillator unit according to claim 1, wherein the three or more electrode wiring boards are arranged along the longitudinal direction of the rod shape.

5. The ultrasonic oscillator unit according to claim 1, further comprising:
three or more cable wiring boards each including a cable wiring part to which the plurality of cables are connected,
wherein respective cable wiring parts of the three or more cable wiring boards and the three or more electrode wiring boards are respectively connected to each other by the three or more connectors.

6. The ultrasonic oscillator unit according to claim 5, wherein the circular-arc backing material layer has an outer surface having a circular-arc cross-section on the rear surface of the ultrasonic oscillator array and has a recess on a side opposite to the outer surface, and
wherein at least portions of the three or more connectors are disposed within the recess of the circular-arc backing material layer.

7. The ultrasonic oscillator unit according to claim 6, wherein the circular-arc backing material layer has a semicircular columnar shape, a shape obtained by cutting a column with a plane parallel to a centerline of the column, a semicylindrical shape, or a bow shape, and
wherein a bottom surface of the circular-arc backing material layer is one continuous plane located on a same plane or two separated planes located on the same plane.

8. The ultrasonic oscillator unit according to claim 6, wherein the recess of the circular-arc backing material layer is provided from an outer side surface of the circular-arc backing material layer in the width direction thereof toward a center side thereof in the width direction.

9. The ultrasonic oscillator unit according to claim 7, wherein the recess of the circular-arc backing material layer is provided from an outer side surface of the circular-arc backing material layer in the width direction thereof toward a center side thereof in the width direction.

10. The ultrasonic oscillator unit according to claim 6, wherein the recess of the circular-arc backing material layer is either a through-hole penetrating from one outer side surface of two outer side surfaces of the circular-arc backing material layer on both sides in the width direction thereof to another outer side surface thereof, or a counterbore recessed from at least one outer side surface of the circular-arc backing material layer in the width direction thereof toward the center side thereof in the width direction.

11. The ultrasonic oscillator unit according to claim 1, wherein the circular-arc backing material layer has an outer surface having a circular-arc cross-section on the rear surface of the ultrasonic oscillator array and has a recess on a side opposite to the outer surface, and wherein at least portions of the three or more connectors are disposed within the recess of the circular-arc backing material layer.

12. The ultrasonic oscillator unit according to claim 11, wherein the recess of the circular-arc backing material layer is provided from an outer side surface of the circular-arc backing material layer in the width direction thereof toward a center side thereof in the width direction.

13. The ultrasonic oscillator unit according to claim 11, wherein two connectors of the three or more connectors are respectively disposed on two outer side surface sides on both sides in the width direction of the circular-arc backing material layer, within the recess of the circular-arc backing material layer, and wherein one or more remaining connectors of the three or more connectors are disposed between the two connectors within the recess of the circular-arc backing material layer.

14. The ultrasonic oscillator unit according to claim 11, further comprising:

a filler layer, made of a heat-conduction member, which covers at least portions of the three or more electrode wiring boards, the three or more connectors, and the plurality of cables.

15. The ultrasonic oscillator unit according to claim 11, wherein the circular-arc backing material layer has a bottom surface that is a most rear surface side portion of the circular-arc backing material layer, and wherein at least portions of the three or more connectors are disposed within the recess of the circular-arc backing material layer and an ultrasonic oscillator array side from the bottom surface.

16. The ultrasonic oscillator unit according to claim 11, wherein the circular-arc backing material layer has a semicircular columnar shape, a shape obtained by cutting a column with a plane parallel to a centerline of the column, a semicylindrical shape, or a bow shape, and wherein a bottom surface of the circular-arc backing material layer is one continuous plane located on a same plane or two separated planes located on the same plane.

17. The ultrasonic oscillator unit according to claim 11, wherein the recess of the circular-arc backing material layer is provided from an outer side surface of the circular-arc backing material layer in the width direction thereof toward a center side thereof in the width direction.

18. The ultrasonic oscillator unit according to claim 11, wherein the recess of the circular-arc backing material layer is either a through-hole penetrating from one outer side surface of two outer side surfaces of the circular-arc backing material layer on both sides in the width direction thereof to another outer side surface thereof, or a counterbore recessed from at least one outer side surface of the circular-arc backing material layer in the width direction thereof toward the center side thereof in the width direction.

19. The ultrasonic oscillator unit according to claim 18, wherein the through-hole has a cross-sectional shape hollowed out in a rectangular shape, a polygonal shape, or a circular shape, wherein the counterbore is formed from at least one outer side surface of the circular-arc backing material layer in the width direction thereof toward the center side thereof in the width direction, and wherein the counterbore is a rectangular counterbore, a polygonal counterbore, a bow-shaped counterbore, a semicircular counterbore, a pyramidal counterbore, or a conical counterbore.

20. The ultrasonic oscillator unit according to claim 11, further comprising:

a filler layer, made of a heat-conduction member, which fills a gap of the recess between at least one connector of the three or more connectors, the three or more electrode wiring boards, and the plurality of cables, which are housed in the recess of the circular-arc backing material layer, and the circular-arc backing material layer.

21. The ultrasonic oscillator unit according to claim 20, wherein, in a case where an acoustic impedance of the filler layer is defined as Zp and an acoustic impedance of the circular-arc backing material layer is defined as Zb, an acoustic impedance reflectivity Q between the filler layer and the circular-arc backing material layer, which is expressed using the following Equation (1) is 50% or less, $$Q = 100 \times |Zp - Zb|/(Zp + Zb) \qquad (1)$$

here, the unit of the acoustic impedance Zp and Zb is $kg/(m^2 \cdot s)$.

22. The ultrasonic oscillator unit according to claim 20, wherein a thermal conductivity of the filler layer is equal to or more than 1.0 W/m·K.

* * * * *